US011155513B2

(12) United States Patent
Abu-Omar et al.

(10) Patent No.: US 11,155,513 B2
(45) Date of Patent: Oct. 26, 2021

(54) EXTRACTION OF NATURAL FERULATE AND COUMARATE FROM BIOMASS

(71) Applicant: SPERO RENEWABLES, LLC, Goleta, CA (US)

(72) Inventors: Mahdi M. Abu-Omar, Goleta, CA (US); Daniel H. Coller, Goleta, CA (US); Ian M. Klein, Goleta, CA (US)

(73) Assignee: SPERO RENEWABLES, LLC, Goleta, CA (US)

( * ) Notice: Subject to any disclaimer, the term of this patent is extended or adjusted under 35 U.S.C. 154(b) by 0 days.

(21) Appl. No.: 16/606,643

(22) PCT Filed: Apr. 20, 2018

(86) PCT No.: PCT/US2018/028566
§ 371 (c)(1),
(2) Date: Oct. 18, 2019

(87) PCT Pub. No.: WO2018/195422
PCT Pub. Date: Oct. 25, 2018

(65) Prior Publication Data
US 2020/0181060 A1   Jun. 11, 2020

Related U.S. Application Data

(60) Provisional application No. 62/487,911, filed on Apr. 20, 2017.

(51) Int. Cl.
| | | |
|---|---|---|
| *C07C 67/56* | (2006.01) | |
| *B01D 11/02* | (2006.01) | |
| *B01D 15/08* | (2006.01) | |
| *C07C 51/09* | (2006.01) | |
| *C07C 51/47* | (2006.01) | |
| *C07C 51/48* | (2006.01) | |
| *C07C 67/58* | (2006.01) | |

(52) U.S. Cl.
CPC ............ *C07C 67/56* (2013.01); *B01D 11/028* (2013.01); *B01D 11/0288* (2013.01); *B01D 11/0292* (2013.01); *B01D 15/08* (2013.01); *C07C 51/09* (2013.01); *C07C 51/47* (2013.01); *C07C 51/48* (2013.01); *C07C 67/58* (2013.01)

(58) Field of Classification Search
CPC ........ A61K 36/00; C07C 27/34; C07C 37/80; C07C 45/80; C07C 67/56; C07C 51/09; C07C 51/47; C07C 51/48; C07C 67/58; B01D 11/028; B01D 11/0288; B01D 11/0292; B01D 15/08
See application file for complete search history.

(56) References Cited

U.S. PATENT DOCUMENTS

| | | | |
|---|---|---|---|
| 3,354,143 A * | 11/1967 | Minoru Takubo ..... | A61K 35/02 514/549 |
| 4,038,481 A * | 7/1977 | Antrim .................... | C08B 1/00 536/56 |
| 4,100,016 A * | 7/1978 | Diebold ................... | D21C 3/20 162/16 |
| 4,514,532 A | 4/1985 | Hsu et al. | |
| 4,764,596 A | 8/1988 | Lora et al. | |
| 4,808,426 A * | 2/1989 | Strop ........................ | C11B 1/00 426/417 |
| 5,128,253 A | 7/1992 | Labuda et al. | |
| 5,169,497 A | 12/1992 | Sarkar et al. | |
| 5,288,902 A * | 2/1994 | Taniguchi ............... | C07C 51/09 562/478 |
| 5,516,923 A | 5/1996 | Hebert et al. | |
| 5,530,112 A * | 6/1996 | Greenshields .......... | A61L 15/28 536/123.1 |
| 5,552,167 A * | 9/1996 | Taylor ..................... | A23D 9/00 426/302 |
| 5,681,427 A | 10/1997 | Lora et al. | |
| 5,843,499 A * | 12/1998 | Moreau ................... | A23D 9/007 426/2 |
| 5,869,708 A | 2/1999 | Das et al. | |
| 5,985,344 A * | 11/1999 | Cherukuri ................ | A23D 9/02 426/417 |
| 6,197,357 B1 * | 3/2001 | Lawton .................... | C11B 3/06 426/330.6 |
| 6,235,507 B1 | 5/2001 | Muheim et al. | |
| 6,352,845 B1 | 3/2002 | Buchanan et al. | |
| 6,495,140 B1 * | 12/2002 | Collins ................ | A61K 36/899 424/745 |

(Continued)

FOREIGN PATENT DOCUMENTS

| | | |
|---|---|---|
| CN | 103254064 A | 8/2013 |
| CN | 103254993 A | 8/2013 |

(Continued)

OTHER PUBLICATIONS

R. Moreau, 44 J. Agric. Food Chem. (1996) (Year: 1996).*
The NEED Project Intermediate Energy Infobook (2016) (Year: 2016).*
R. Norton et al., Quantitation of Steryl Ferulate and p-Coumarate Esters from Corn and Rice, 30 Lipids (1995) (Year: 1995).*
K. Tekin et al., 40 Renewable and Sustainable Energy Reviews, 673-687 (2014) (Year: 2014).*
J. Kanski et al., 13 Journal of Nutritional Biochemistry, 273-281 (2002) (Year: 2002).*
N.G. Anderson, Practical Process & Research Development, 113-143 (2000) (Year: 2000).*
Leonard et al., Advanced Practical Organic Chemistry 128-226 (2nd ed., 1995) (Year: 1995).*
M. Patel et al., 63 Journal of Scientific & Industrial Research, 569-578 (2004) (Year: 2004).*

(Continued)

*Primary Examiner* — Alexander R Pagano
(74) *Attorney, Agent, or Firm* — Andrew M. Metrailer

(57) ABSTRACT

A process for a reactive separation of organic molecules from biomass includes a reaction step for the biomass, a simultaneous extraction step using a solvent, and a filtration step to recover products, wherein the products comprise ferulic acid and/or coumaric acid. The products are extracted from the biomass in a pressurized stirred batch reactor using a liquid extraction solvent and a base in which the ferulate and the coumarate remain.

28 Claims, 11 Drawing Sheets

(56) References Cited

U.S. PATENT DOCUMENTS

| | | | |
|---|---|---|---|
| 6,844,019 B1* | 1/2005 | Cheetham | C12P 7/42 |
| | | | 426/534 |
| 7,368,138 B2* | 5/2008 | Abbas | A61K 36/899 |
| | | | 424/750 |
| 7,462,470 B2 | 12/2008 | Sun et al. | |
| 7,465,791 B1 | 12/2008 | Hallberg et al. | |
| 7,833,994 B2 | 11/2010 | Abbas et al. | |
| 8,114,447 B2 | 2/2012 | Abbas et al. | |
| 8,361,764 B1 | 1/2013 | Wong et al. | |
| 9,452,422 B2 | 9/2016 | Kellett et al. | |
| 9,637,765 B2 | 5/2017 | Luterbacher et al. | |
| 9,714,299 B2 | 7/2017 | Bonde | |
| 9,718,742 B2 | 8/2017 | Sharma et al. | |
| 10,202,328 B2* | 2/2019 | Revelant | C12P 7/62 |
| 2002/0048613 A1* | 4/2002 | Romanczyk, Jr. | A23D 9/02 |
| | | | 424/776 |
| 2002/0114853 A1* | 8/2002 | Krasutsky | B01D 11/0219 |
| | | | 424/725 |
| 2003/0017221 A1* | 1/2003 | Antrim | D21C 5/005 |
| | | | 424/750 |
| 2003/0235633 A1* | 12/2003 | Abbas | A61K 36/899 |
| | | | 424/750 |
| 2005/0042172 A1* | 2/2005 | Whittle | A61P 43/00 |
| | | | 424/46 |
| 2005/0238738 A1* | 10/2005 | Lee | A61K 36/88 |
| | | | 424/757 |
| 2009/0023182 A1* | 1/2009 | Schilling | C12P 39/00 |
| | | | 435/42 |
| 2009/0155866 A1* | 6/2009 | Burk | C07C 67/333 |
| | | | 435/135 |
| 2009/0308041 A1* | 12/2009 | Whitelaw | A23D 9/00 |
| | | | 56/126 |
| 2011/0086116 A1* | 4/2011 | Florence | A61P 17/18 |
| | | | 424/739 |
| 2011/0086149 A1* | 4/2011 | Bootsma | C10L 1/026 |
| | | | 426/541 |
| 2012/0196332 A1* | 8/2012 | Muniglia | C12Y 302/01023 |
| | | | 435/99 |
| 2014/0271928 A1* | 9/2014 | Rehage | A01N 59/08 |
| | | | 424/680 |
| 2015/0224485 A1 | 8/2015 | McGuire | |
| 2016/0145183 A1* | 5/2016 | Revelant | C07C 51/00 |
| | | | 435/135 |
| 2016/0289150 A1 | 10/2016 | Delgass et al. | |
| 2017/0152278 A1 | 6/2017 | Samec et al. | |
| 2018/0280459 A1* | 10/2018 | Eyal | A61K 36/185 |

FOREIGN PATENT DOCUMENTS

| | | | |
|---|---|---|---|
| CN | 103319328 A | 9/2013 | |
| CN | 103553902 A | 2/2014 | |
| CN | 103553903 A | 2/2014 | |
| EP | 0817824 A2 * | 1/1998 | C07H 1/08 |
| EP | 0817824 B1 | 1/1998 | |
| WO | 2012155074 A1 | 11/2012 | |
| WO | 2015023583 A2 | 2/2015 | |
| WO | 2017178513 A1 | 10/2017 | |
| WO | 2018195422 A1 | 10/2018 | |
| WO | 2019108959 A1 | 6/2019 | |

OTHER PUBLICATIONS

R. Moreau et al., 44 J. Agric. Food Chem., 2149-2154 (1996) (Year: 1996).*

R. Moreau et al., 76 Cereal Chem., 449-451 (1999) (Year: 1999).*

R. Moreau et al., 80 JAOCS, 1063-1067 (2003) (Year: 2003).*

J. Chien et al., 43 The Chemical Engineering Journal (1990) (Year: 1990).*

R. Moreau et al., 81 JAOCS, 1071-1075 (2004) (Year: 2004).*

J. Kwiatkowski et al., 79 JAOCS, 825-830 (2002) (Year: 2002).*

R. Moreau et al., 82 JAOCS, 809-815 (2005) (Year: 2005).*

Foreign Communication from a Related Counterpart—International Search Report and Written Opinion, dated Jul. 8, 2018, PCT Application No. PCT/US20181028566, filed on Apr. 20, 2018.

Foreign Communication from a Related Counterpart—International Search Report and Written Opinion, dated Mar. 15, 2019, PCT Application No. PCT/US2018/063351, filed on Nov. 30, 2018.

G. Remaud, et al. Detection of Sophisticated Adulterations of Natural Vanilla Flavors and Extracts: Application of the SNIF-NMR Mehtod to Vanillin and p-Hydroxybenzaldehyde, Journal of Agricultural and Food Chemistry 45 (1997) 859-866.

E. Tenailleau, et al. Autentication of the Origin of Vanillin Using Quantitative Natural Abudnacnce 13C NMR, Journal of Agricultural and Food Chemistry 52 (2004) 7782-7787.

D.J. Rose, G.E. Inglett, S.X. Liu, Utilisation of corn (Zea mays) bran and corn fiber in the production of food components, Journal of the science of food and agriculture 90 (2010) 915-924.

A. Lygin, J. Upton, F Dohleman, J. Juvik, O. Zabotina, J. Widholm, V. Lozovaya, Composition of cell wall phenolics and polysaccharides of the potential bioenergy crop—Miscanthus, GCB Bioenergy 3 (2011) 333-345.

Raquez, J. M.; Deleglise, M.; Lacrampe, M. F.; Krawczak, P., Thermosetting (bio)materials derived from renewable resources: A critical review. Prog. Polym. Sci. 2010, 35, 487-509. https://doi.org/10.1016/j.progpolymsci.2010.01.001.

Foreign Communication from a Related Counterpart—International Preliminary Report on Patentability, dated Oct. 31, 2019, PCT Application No. PCT/US2018/028566, filed on Apr. 20, 2018.

Foreign Communication from a Related Counterpart—International Preliminary Report on Patentability, dated Jun. 11, 2020, PCT Application No. PCT/US2018/063351, filed on Nov. 30, 2018.

* cited by examiner

Ethyl ester of linoleic acid

Ethyl ester of oleic acid

EXTRACTION OF NATURAL FERULATE AND COUMARATE FROM BIOMASS

CROSS-REFERENCE TO RELATED APPLICATIONS

This application is a filing under 35 U.S.C. 371 as the National Stage of International Application No. PCT/US2018/028566, filed on Apr. 20, 2018, entitled, "EXTRACTION OF NATURAL FERULATE AND COUMARATE FROM BIOMASS," which claims the benefit of and claims priority to U.S. Provisional Application No. 62/487,911, filed on Apr. 20, 2017 and entitled "Extraction of Natural Ferulate and Coumarate from Biomass", both of which are incorporated herein by reference in their entirety for all purposes.

STATEMENT REGARDING FEDERALLY SPONSORED RESEARCH OR DEVELOPMENT

This invention was made with Government support under grant number 1647923 awarded by the U.S. National Science Foundation Phase I SBIR. The government has certain rights in the invention.

REFERENCE TO A MICROFICHE APPENDIX

Not applicable.

BACKGROUND

Ferulic acid (3-(4-hydroxy-3-methoxy-phenyl)prop-2-enoic acid, 3-(4-hydroxy-3-methoxyphenyl)acrylic acid) is a powerful anti-oxidant used in consumer products and pharmaceuticals. The flavor and fragrance industry transforms ferulic acid to vanillin using enzymatic processes [see for example, I. Labuda, et al. (Kraft Foods Inc) U.S. Pat. No. 5,128,253A (1991); A. Muheim, et al. (Givaudan Roure (International) SA), U.S. Pat. No. 6,235,507 B1 (1997)]. Natural vanillin produced from natural ferulic acid is of particular importance due to the volatility, high cost, and scarcity of natural vanilla extract derived from vanilla beans.

SUMMARY

In an embodiment, a process for a reactive separation of organic molecules from biomass comprises a reaction step for the biomass, a simultaneous extraction step using a solvent, and a filtration step to recover products, wherein the products comprise a ferulate or a coumarate. The products are extracted from the biomass in a pressurized stirred batch reactor using a liquid extraction solvent and a base in which the ferulate and the coumarate remain.

In an embodiment, a reactive separation process for a separation of organic molecules including acidic esters, terpenoids, sterols, carbohydrates, and flavonoids from biomass, the process comprises a reaction step using a base in contact with the biomass, a simultaneous solvent extraction step using a solvent, and a filtration step to recover products comprising the organic molecules.

In an embodiment, a process to extract a ferulate and a coumarate from agricultural biomass in a packed bed reactor comprises contacting the biomass with a solvent and a base in the packed bed reactor, wherein the agricultural biomass acts as a stationary bed.

These and other features will be more clearly understood from the following detailed description taken in conjunction with the accompanying drawings and claims.

BRIEF DESCRIPTION OF THE DRAWINGS

For a more complete understanding of the present disclosure and the advantages thereof, reference is now made to the following brief description, taken in connection with the accompanying drawings and detailed description.

DETAILED DESCRIPTION

Figure 1:
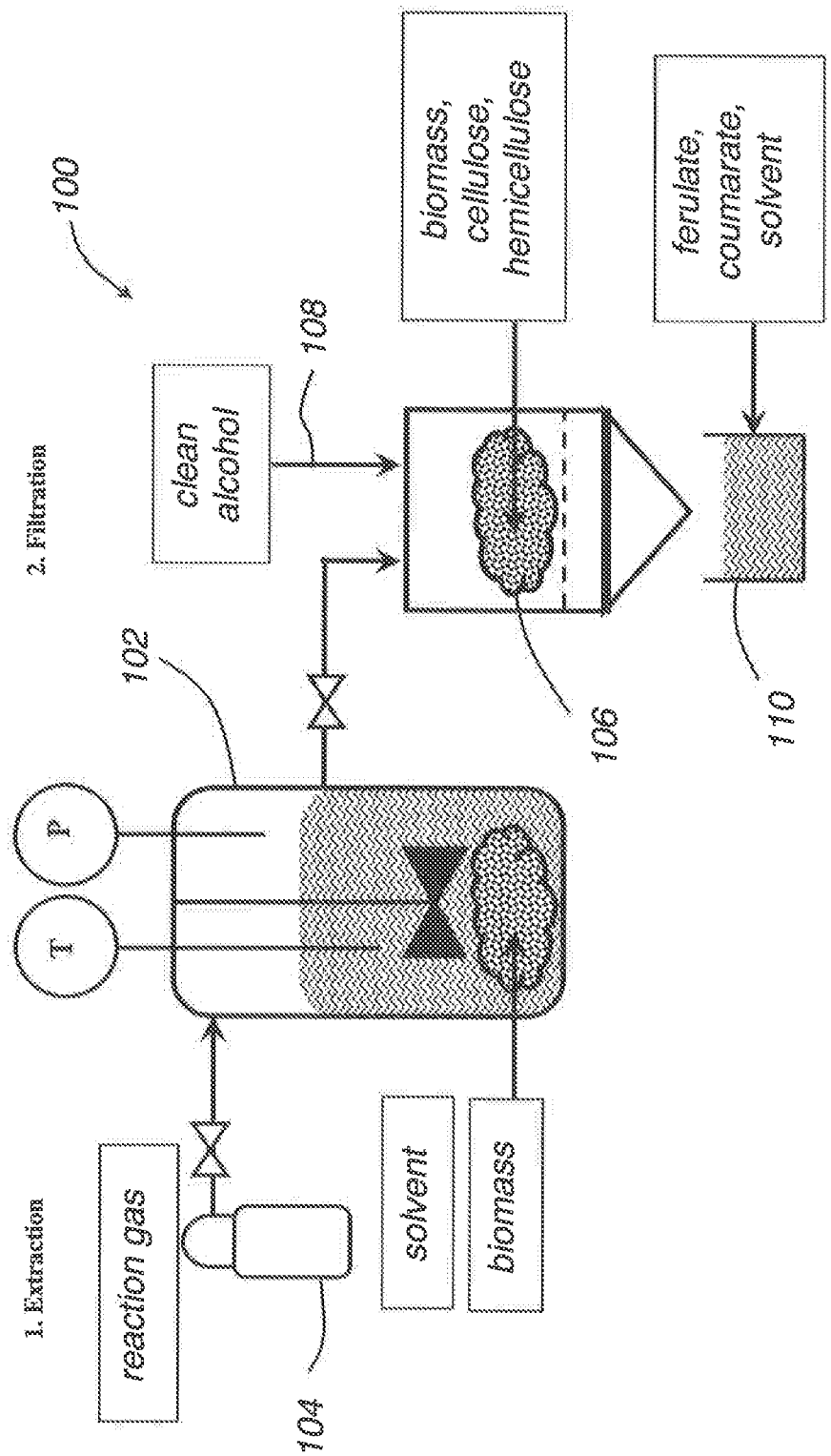
FIG. 1 is a schematic process illustration of a stirred batch reactor according to an embodiment.

Ferulic and coumaric acid are powerful anti-oxidants. Ferulic acid is also used in the flavor and fragrance industry to produce natural vanillin. Disclosed herein a process for the extraction of ferulate (ferulic acid ester) and coumarate (coumaric acid ester) from agricultural biomass containing ferulic and coumaric acid linkages is described. The extracted ferulate and coumarate can be classified as natural, for example following European 1334/2008 and US Food and Drug administration (FDA) 21CFR101.22 regulations regarding natural labeling. The extracted ferulate can be hydrolyzed to ferulic acid in the extraction mixture, or hydrolyzed after separation. Additional cinnamic acids, sugars, corn oil and fatty acids are also extracted during the process.

Consumer demands for natural products and ingredients have driven the industry to seek new sources of natural vanilla, while vanilla derived from synthetic, non-natural sources such as petrochemicals and eugenol have seen a decrease in demand. Carbon 13 NMR of vanillin is used to determine the source of vanillin by the ratio of $^{13}C$ and $^{12}C$ at the eight carbons of vanillin, with the carbons of the aldehyde and the methoxy group determined to be the most important [G. Remaud, et al. (J. Ag. Food Chem.) 45 (1997); E. Tenailleau, et al. (J. Ag. Food. Chem.) 52 (2004)]. Synthetic sources such as guaiacol can be discriminated from natural vanillin sourced from beans and ferulic acid, with thresholds dependent on the experimental setup.

Much of the supply of natural ferulic acid is extracted during the processing of rice bran oil [see, for example, H. Taniguchi, et al. (Wakayama, JP) U.S. Pat. No. 5,288,902 (1994); Z. Sun, et al. (Zhejiang Hangzhou Xinfu Pharmaceutical Co., Ltd) U.S. Pat. No. 7,462,470 (2006); CN 103553903A; CN 103553902A; CN 103254993B,]. Ferulic acid is also contained in agricultural biomass such as miscanthus, corn byproducts (fiber, bran, stover, fines, gluten feed, etc.), rice, wheat, beets, beet fiber, beet pulp, and other crops. Typical methods for extracting ferulic acid include alkali extraction [R. Antrim, et al. (Standard Brands Incorporated), U.S. Pat. No. 4,038,481 (1977); A. Muir, Westcott, N. (CA Minister Agriculture & Food) EP 0817824B1 (2001); CN 103254064B (2015); CN 103319328B (2015)] and enzymatic processes [D. Wong, et al. (US Department of Agriculture), U.S. Pat. No. 8,361,764 B1 (2013); C. Buchanan, et al. (Eastman Chemical Co), U.S. Pat. No. 6,352,845 B1 (2002)]. Alternatively, ferulic acid is extracted as several ferulic acid phytosterol esters such or γ-oryzanol [C. Abbas, et al. (Archer Daniels Midland Co) US 20030235633 A1 (2003); C. Abbas, et al. (Archer Daniels Midland Co) U.S. Pat. No. 7,833,994B2 (2010); R. Moreau, et al. (US Department of Agriculture) U.S. Pat. No. 5,843,499A (1998); P. Das, et al. (Council of Scientific and Industrial Research) U.S. Pat. No. 5,869,708A (1999)]. Excess alcohol extraction has been used to remove lignin from biomass [V. Diebold, et al. (Alcell Technologies Inc.) U.S. Pat. No. 4,100,016A (1978)], and similar extractions have been used to extract ferulic acid esters. For example, in the presence of methanol, the extract contains methyl ferulate (methyl 3-(4-hydroxy-3-methoxyphenyl)acrylate), while in the presence of ethanol the extract contains ethyl ferulate (ethyl 3-(4-hydroxy-3-methoxyphenyl)acrylate). Naturally derived ferulate can be transformed into natural ferulic acid via alkaline hydrolysis.

This application describes a process for extracting ferulate (ferulic acid esters of the variety methyl-, ethyl-, propyl-, butyl-, or any variation thereof) and coumarate from agricultural biomass such as miscanthus and corn byproducts. The extraction can be carried out in either batch or continuous operation. Under conditions compatible with cooking procedures, the extracted ferulic acid can be marketed as natural in the European Union and the United States. For example, the extracted products can be marked as natural following European 1334/2008 and/or US Food and Drug administration (FDA) 21CFR101.22 regulations regarding natural labeling. Ferulate can be hydrolyzed to ferulic acid.

As disclosed herein, a process for extracting ferulate and coumarate can include a reaction step and/or extraction step for the extraction of ferulates and coumarates from biomass. A filtration step can be used to recover the products. The reaction step, which can occur prior to or simultaneously with the extraction step, can occur with a base. The extraction step can occur in the presence of a solvent. The products can comprise at least one of: ferulate (ferulic acid ester), and coumarate (coumaric acid ester).

Figure 3:
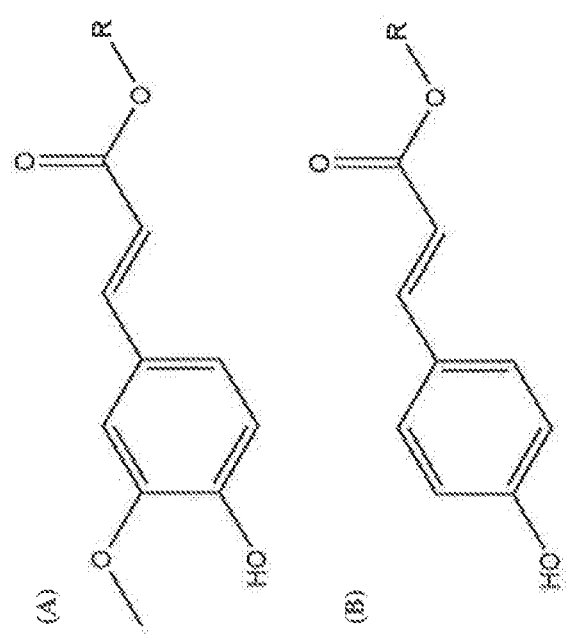
FIG. 3 illustrates the chemical structure or ferulic acid, various ferulates, coumaric acid, and various coumarates.

The present process is related to the extraction of ferulates (ferulic acid esters) and optionally coumarates from agricultural biomass. The structures of exemplary ferulates and coumarates are shown in FIG. 3. As shown in FIG. 3(A), R can represent a hydrogen or an alkyl group such that: ferulic acid: R=H, methyl ferulate: R=$CH_3$, ethyl ferulate: R=$C_2H_5$, propyl ferulate: R=$C_3H_7$, butyl ferulate: R=$C_4H_9$. As shown in FIG. 3(B) R can represent a hydrogen or an alkyl group such that: coumaric acid: R=H, methyl coumarate: R=$CH_3$, ethyl coumarate: R=$C_2H_5$, propyl coumarate: R=$C_3H_7$, butyl coumarate: R=$C_4H_9$.

In the present application, any suitable biomass can be used as a starting stock. Various exemplary biomass feedstocks can include, but are not limited to, miscanthus, corn bran, corn fiber, corn gluten feed, distillers' grain, corn stover, corn gluten meal, beet fiber, rice hulls, and/or other agricultural residues.

The process can include an extraction step using a solvent. In some embodiments, the solvent can comprise an alcohol (e.g., an organic alcohol) along with a co-solvent such as water. While not wishing to be limited by theory, it has been noted that the identity of the ferulate is directly linked to the chosen alcohol in the solvent. For example, the use of methanol yields methyl ferulate and the use of ethanol yields ethyl ferulate. Esters of coumaric acid are simultaneously extracted. In some embodiments, the extraction solvent can comprise 0-50% water and a pure aliphatic alcohol or mixtures of aliphatic alcohols (e.g., methanol, ethanol, n-propanol, iso-propylalcohol, n-butanol, 2-butanol, tert-butanol, n-pentanol, etc.), where the aliphatic alcohol can comprise 50-100% of the solvent. In some embodiments, the solvent may include only water and one or more aliphatic alcohols. In still other embodiments, water may not be present in the solvent, and rather 100% alcohol of the variety methanol or ethanol can be used for the solvent. When ethanol is biologically obtained (e.g., produced from fermentation, etc.), ethyl ferulate can be labeled as natural when using such ethanol as the solvent in the extraction. In some instances, the products can be considered natural when all of the carbons in the products (e.g., in the ethyl ferulate, etc.) are naturally sourced.

In some embodiments, a reaction step can also be carried out using a base. This reaction step can be carried out at the same time as the extraction. For example, base can be added to the solvent to enhance solubility and rate of extraction at lower reaction temperatures. Bases include any first or second group hydroxides such as sodium hydroxide or potassium hydroxide, carbonates, bicarbonates, and ammonium in concentrations of about 0 to about 1 N (molar equivalents of base per liter of solvent). For example, the concentration of the base can be between 0.01 and about 0.1 N, or between about 0.02 and about 0.06 N, or about 0.04 N.

Various process designs can be used to carry out the extraction and/or reaction steps. Any suitable reactor configuration capable of contacting the biomass feedstock with the solvent and/or base can be used. For example, a batch reactor and/or a continuous flow reactor can be used. FIG. 1 illustrates a process 100 for the extraction of ferulates and/or coumarates from biomass using a batch reactor such as a stirred batch reactor 102. Under stirred batch reaction conditions, the starting materials (e.g., the solvent including an alcohol with or without water, optionally a base, and the biomass) can be mixed together in a stirred batch reactor 102 and sealed shut. Alternatively, the biomass, solvent(s), and base can be pre-mixed as a slurry and fed into the reactor 102 using a pump or gravity. The mass to mass ratio for solvent:biomass can be in the range of about 4 to about 20. In some embodiments, the mass to mass ratio for solvent:biomass of about 10 to about 15 can be used. The reaction atmosphere can be purged of oxygen using an inert gas from an inert gas source 104 such that the atmosphere is inert with argon, helium, nitrogen, or a mixture thereof. Hydrogen (0-100%) atmospheres give similar results to a purely inert atmosphere. The purge gas can also be used to pressurize the reactor 102. The reactor 102 can be pressurized to between about 1 to about 3 bar at room temperature, with about 1 bar preferred. The reactor 102 can be heated at 100-300° C. $hr^{-1}$ (e.g., between about 200° C. $hr^{-1}$ to about 300° C. $hr^{-1}$, or about 300° C. $hr^{-1}$ to a dwell temperature of between about 80° C. and about 250° C., or between about 100° C. to 250° C. The reactor 102 can maintain the maximum extraction temperature for between 1-15 hours, for example for about 12 hours. The stirring mechanism can be operated from about 100 to about 600 rpm, for example, about 200 rpm.

After reaction, the reactor 102 can be cooled to room temperature. The reactor 102 can be purged to atmospheric pressure. The solid/liquid post reaction slurry 106 can be removed from the reactor 102 either by pump or by gravity and filtered for solids. The solid residue can be rinsed with clean solvent 108 using 50%-150% the volume of the filtered solids. The wet solids can then be pressed to further remove liquid captured in the solids. The resulting products 110 can then be captured for further processing.

Figure 2:
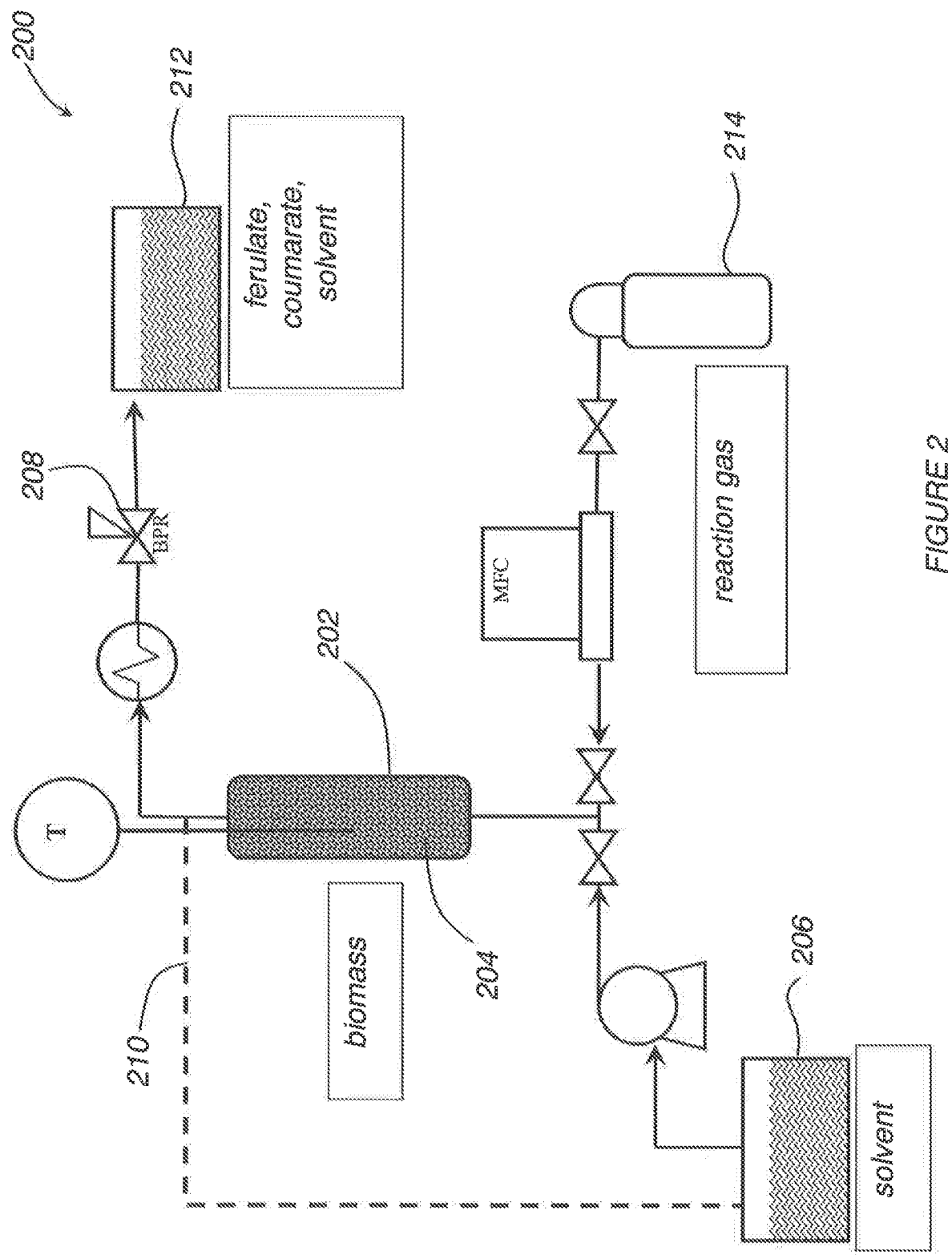
FIG. 2 is a schematic process illustration of a continuous extraction process using a packed bed reactor according to an embodiment.

FIG. 2 illustrates a continuous extraction reactor scheme 200 for the extraction and/or reaction of the biomass to remove ferulates and/or coumarates. As shown in FIG. 2, a packed bed reactor 202 can be used to continuously extract ferulate from agricultural biomass 204. In this configuration, the agricultural biomass bed 204 acts as the stationary bed. Heated and pressurized solvent 206 can be pumped over the biomass bed 204, which extracts ferulate and coumarate. A back pressure regulator 208 downstream from the packed bed maintains the reactor 202 at a steady pressure, typically between about 1 to about 30 bar. The typical operating conditions can include a bed temperature of between about 80° C. and about 250° C., a reactor pressure of between about 1 and about 30 bar. The solvent flow rate may be suitable for the reactor conditions and can have an liquid hourly space velocity of about 0.06 $hr^{-1}$ to 0.6 $hr^{-1}$. The reactor 202 could be operated such that the extraction solvent either enters the biomass bed 204 a single time or is recycled through the reactor several times. For example, optional recycle line 210 can be used to recycle the solvent for recycle through the packed biomass bed 204. The extraction solvent 206 can be collected in a reservoir 212 at the exit of the reactor 202.

During operation, the reactor 202 can be purged and pressurized with an inert gas from an inert gas source 214. The temperature of the reactor 202 can then be ramped up at a rate of between about 100 and about 300° C. $hr^{-1}$ to the desired operating temperature. After reaching reaction temperature, the reactor 202 can be operated for between about 2-8 hours. The reactor 202 can then be cooled and the flow of solvent briefly increased to wash the biomass bed 204. The solvent flow can be stopped after the reactor temperature decreases to approximately 20-40° C. The pressure can be returned to atmospheric pressure after the reactor 202 reaches room temperature. The spent biomass can then be emptied from the reactor 202.

Figure 4:
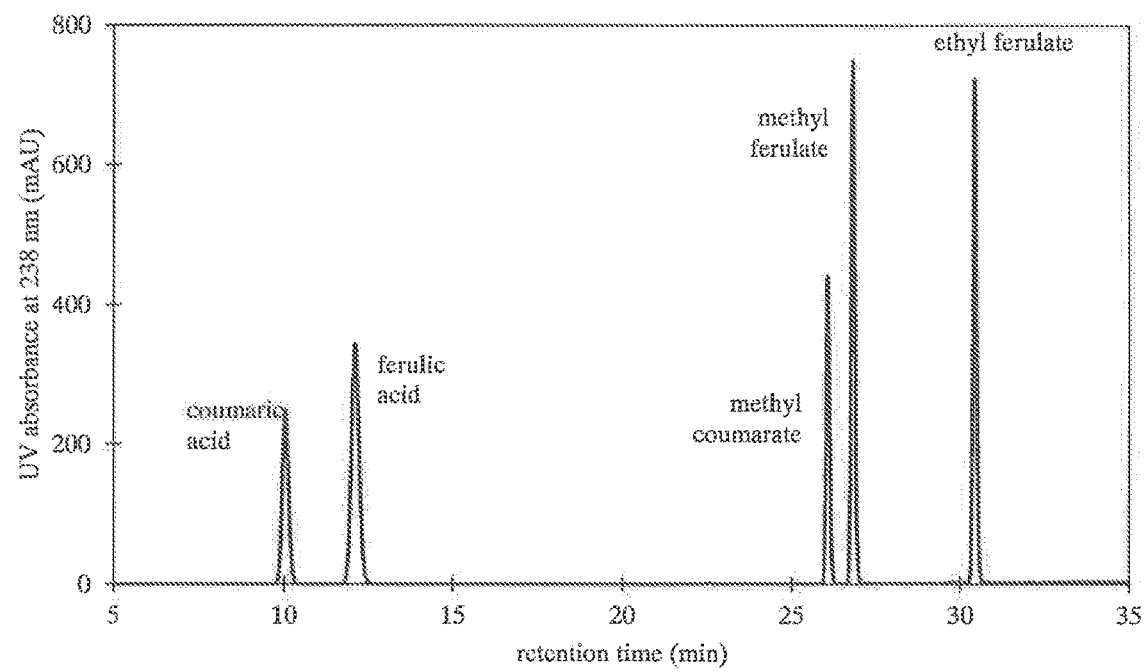
FIG. 4 illustrates the results of an HPLC/UV-vis chromatogram.

The resulting products can be characterized through testing. For example, the liquid product stream can be analyzed with a HPLC equipped with a UV-vis detection. The column is a Zorbax SB-Phenyl reversed-phase C18 HPLC column. Two methods can be used to quantify the mass of ferulate, coumarate, coumaric acid, and ferulic acid in the liquid product. In Method 1, a gradient of water and acetonitrile can be used to elute the products at 30° C. and a flow rate of 0.5 mL $min^{-1}$. In Method 2, a gradient of 1 mM of aqueous trifluoroacetic acid and acetonitrile elute the products at 30° C. and a flow rate of 1.0 mL $min^{-1}$. Ferulate and coumarate can be quantified by Method 1 or 2. Ferulic acid and coumaric acid can only be quantified by Method 2, although ferulic acid and coumaric acid are visible using Method 1, the peaks, however, are not well resolved. FIG. 4 shows a HPLC chromatogram for chemical standards of ferulic acid, coumaric acid, methyl ferulate, methyl coumarate, and ethyl ferulate. As shown in FIG. 4, methanol was injected which contained 1.02, 1.00, 1.07, 1.08, and 1.03 mM of coumaric acid (10.0 min), ferulic acid (12.1 min), methyl coumarate (26.1 min), methyl ferulate (26.8 min), and ethyl ferulate (30.4 min), respectively. Standard curves for each ferulate and coumarate were created to determine the concentration and yield of each product. The concentration of ferulate and ferulic acid was determined at a wavelength of 238.8 nm while coumarate and coumaric acid were quantified at 310.8 nm. Tests carried out as described herein on products from exemplary reactor runs was used to calculate the total yield (based on the starting mass of dry biomass) of ferulate, and the total yield from each biomass was near the theoretical content as shown in Table 1.

TABLE 1

Theoretical and extracted ferulate content of agricultural biomass

| Biomass | Theoretical ferulic acid content ($g_{ferulic\ acid}/g_{biomass}$) | Extracted ferulate content ($g_{ferulate}/g_{biomass}$) |
|---|---|---|
| Corn bran | 2.8-3.1[1] | 2.6 |
| Corn fiber | 1.0-1.8[1] | 1.6 |
| Corn gluten feed | 1.0-1.8[1] | 0.8 |
| Corn stover |  | 0.4 |
| *Miscanthus* | 0.5-1.0[2] | 0.6 |

A number of additional processing steps can be carried out on the liquid products from the extraction and/or reaction steps. Initially, the ferulate can be concentrated and an oil phase referred to as "corn oil" can be removed. The ferulate in the resulting solution, or alternatively in the liquid products prior to the concentration to the liquid products, can be hydrolyzed to ferulic acid. Lignin and polysaccharides in the resulting liquid phase can be precipitated to further purify the ferulic acid. An organic solvent can then be used to extract the ferulic acid followed by hot filtration and precipitation of a solid ferulic acid product. Additional purification steps can also be carried out to further purify the ferulic acid as desired.

In an embodiment, the ferulate in the liquid product from the extraction and/or reaction steps can be concentrated. Following extraction of ferulate into the basic alcohol solution, an evaporator (e.g., a rotary evaporator, etc.) can be used to concentrate the alcohol/ferulate solution until the alcohol concentration is between about 0% and about 75% of the total solution by mass, or between about 40% and about 50% alcohol by mass. Concentration of the alcohol/ferulate solution can result in a viscous brown oil. Liquid extraction can be used to remove a variety of fatty acid esters comprised of primarily esters of oleic and linoleic acids and referred to herein as the corn oil from the alcohol/ferulate solution. While not wishing to be limited by theory, it has been noted that the identity of the esters of oleic and linoleic acids are directly linked to the chosen alcohol in the solvent. For example, the use of ethanol yields the ethyl esters of oleic and linoleic acids and use of methanol yields the methyl esters of oleic and linoleic acid. Prior to liquid extraction of the corn oil, the concentrated alcohol/ferulate solution can be diluted with a solution of aqueous base. For example, between about 50-300 g aqueous base solution can be added per 100 g concentrated alcohol/ferulate solution. Bases can include any first or second group hydroxides such as sodium hydroxide or potassium hydroxide, carbonates, bicarbonates, and ammonium. In some embodiments, sodium hydroxide can be used in concentrations between 0.1-10 N. Following dilution of the concentrated alcohol/ferulate solution with aqueous base, corn oil is removed by a liquid-liquid extraction with an organic solvent including, but not limited to, pentane, hexane, heptane, cyclohexane, benzene, toluene, diethyl ether, or mixtures thereof. In some embodiments, the organic solvent used in the liquid-liquid extraction is hexane. Corn oil can be recovered by evaporation of the organic solvent used for the liquid-liquid extraction. Extraction of corn oil from the ferulate solution can be completed before and/or after hydrolysis of ferulate to ferulic acid. Extraction of corn oil before hydrolysis can be used to advantageously reduce the processing volume of the hydrolysis step. The extracted corn oil can have a phosphorous content of less than 250 ppm, less than 150 ppm, less than 100 ppm, less than 50 ppm, or less than 25 ppm, all by mass. In some embodiments, the extracted corn oil can contain less than 3 ppm by mass phosphorous. The extracted corn oil can have a free fatty acid content (as oleic acid) of less than about 3% by mass of the oil. In some embodiments the extracted corn oil can have a free fatty acid content (as oleic acid) of less than about 1.5% by mass of the oil.

The liquid solution containing the ferulate can be hydrolyzed before or after removal of the corn oil from the products. The liquid solution can be hydrolyzed under basic conditions to convert at least a portion of the ferulate to ferulic acid. In this process, additional base can be added to the ferulate solution and the solution can then be heated above 20° C. to initialize the hydrolysis. Bases include any first or second group hydroxides such as sodium hydroxide or potassium hydroxide, carbonates, bicarbonates, ammonium, and any combination thereof. The base used can be the same or different than the base used in the initial reaction step with the biomass. In some embodiments, sodium hydroxide can be used as the base, and the sodium hydroxide can be used in concentrations between 0.1-10 N. The mixture can be heated to between about 30-100° C. for about 0.5-5 hours. Under these conditions, ethyl- and methyl ferulate can hydrolyze (e.g., partially hydrolyze, substantially completely hydrolyze, or completely hydrolyze) to ferulic acid.

Once hydrolyzed, the resulting mixture containing the ferulic acid can be treated to precipitate byproducts of the extraction process such as any lignin and polysaccharides. The precipitation process can be carried out by acidifying the ferulic acid containing solution to selectively precipitate lignin and polysaccharides while the ferulic acid remains in solution. The concentration of ferulic acid can be adjusted to between about 1-20 g/L by addition of water to the ferulic acid containing solution, and the solution can be maintained at a temperature of between about 20-100° C. The ferulic acid solution can then be acidified to a pH of between about 3-6 by addition of an acid. Suitable acids useful in the acidification of the ferulic acid solution can include, but are not limited to, hydrochloric acid, nitric acid, phosphoric acid, sulfuric acid, acetic acid, and combinations thereof. In some embodiments the acid can be sulfuric acid. Upon acidification, the by-products can precipitate in the acidified solution. The acidified solution can be filtered to remove the precipitated byproducts including lignin and polysaccharides which precipitate as solid materials. In some embodiments, a powder such as diatomaceous earth, celite, alumina, and/or silica may be added to the ferulic acid solution before acidification. Upon acidification, precipitated byproducts such as lignin and polysaccharides can bind to the inert powder, increasing the ease of filtration and preventing fouling. In some embodiments, centrifugation can be used to isolate the solid precipitated lignin and polysaccharides from the acidified solution in place of filtration.

The acidified solution having at least a portion of the byproducts removed can be further purified using a variety of processing steps. In some embodiments, the ferulic acid can be further purified using an extraction process using an organic solvent. In this step of a purification process, a liquid-liquid extraction can be used to extract ferulic acid from an aqueous solution to an organic solvent. Suitable organic solvents may include, but are not limited to, ethyl acetate, diethyl ether, dichloromethane, hexane, heptane, pentane, toluene, xylenes, and mixtures thereof. In some embodiments, the organic solvent can be or include ethyl acetate. The aqueous solution containing ferulic acid can be further acidified to a pH of between about 1-5 by addition of an acid before extraction with an organic solvent. Suitable acids can include, but are not limited to, hydrochloric acid, nitric acid, phosphoric acid, sulfuric acid, acetic acid, and combinations thereof. In some embodiments, the acid can be or include sulfuric acid. Upon acidification, the aqueous ferulic acid solution can be extracted with the organic solvent using liquid-liquid contact. Typically the volume of organic solvent used to extract the ferulic acid is between about 0.5-3 times the volume of the aqueous ferulic acid solution. Following extraction of the ferulic acid into the organic solvent, the organic solvent phase can separated from the aqueous phase, and the organic solvent can then be removed by evaporation (e.g., rotary evaporation, etc.) to yield solid or semi-solid ferulic acid. In some embodiments, the solid or semi-solid ferulic acid can have a purity of between about 10-50% or between about 20-40% by mass. The resulting ferulic acid can be used as product or subjected to further purification depending on the use and product purity requirements.

The solid or semi-solid ferulic acid can be further purified using a dissolution-precipitation process. In some embodiments, the solid ferulic acid of low purity (e.g., between about 10% to about 50% or between about 20-40% purity by mass) can be further purified through a hot filtration and precipitation process. In this process, the solid ferulic acid can be dissolved in water at a concentration of 1-10 g/L ferulic acid and heated to between about 60-100° C. The heated mixture can be filtered to remove non-soluble materials while maintaining a temperature of between about 60-100° C. The filtrate can then be cooled to precipitate solid ferulic acid at a purity greater than the starting purity. In some embodiments, the dissolution-precipitation process can increase the purity of the solid ferulic acid to between about 60-99% purity by mass. Alternatively the concentration of ferulic acid in the filtrate can be increased from 1-10 g/L to 10-35 g/L by evaporating a portion of the aqueous filtrate prior to cooling to precipitate solid ferulic acid with a purity of between about 60-99% by mass.

Additional purifications processes can be used to purify the solid or semi-solid ferulic acid in addition to the dissolution-precipitation process or in place of the dissolution-precipitation process. In some embodiments, liquid chromatography can be used increase the purity of ferulic acid. In this process, liquid chromatography can be used to increase the purity of ferulic acid from between about 10-50% purity or between about 20-40% purity to about 99% or greater purity if applied before a dissolution-precipitation process. If applied after a dissolution-precipitation process, liquid chromatography can be used to increase the purity of ferulic acid from about 60-99% purity by mass to >99% purity by mass. Liquid chromatography techniques used in this step include but are not limited to: ion exchange chromatography and size exclusion chromatography.

Once purified, the resulting product can include a concentrated ferulic acid solution or solid or semi-solid ferulic acid. The products can then be used for a variety of commercial uses.

EXAMPLES

The disclosure having been generally described, the following examples are given as particular embodiments of the disclosure and to demonstrate the practice and advantages thereof. It is understood that the examples are given by way of illustration and are not intended to limit the specification or the claims in any manner.

Example 1

Example 1. Extraction of Ethyl Ferulate and Ethyl Coumarate from Corn Fiber

Figure 5:
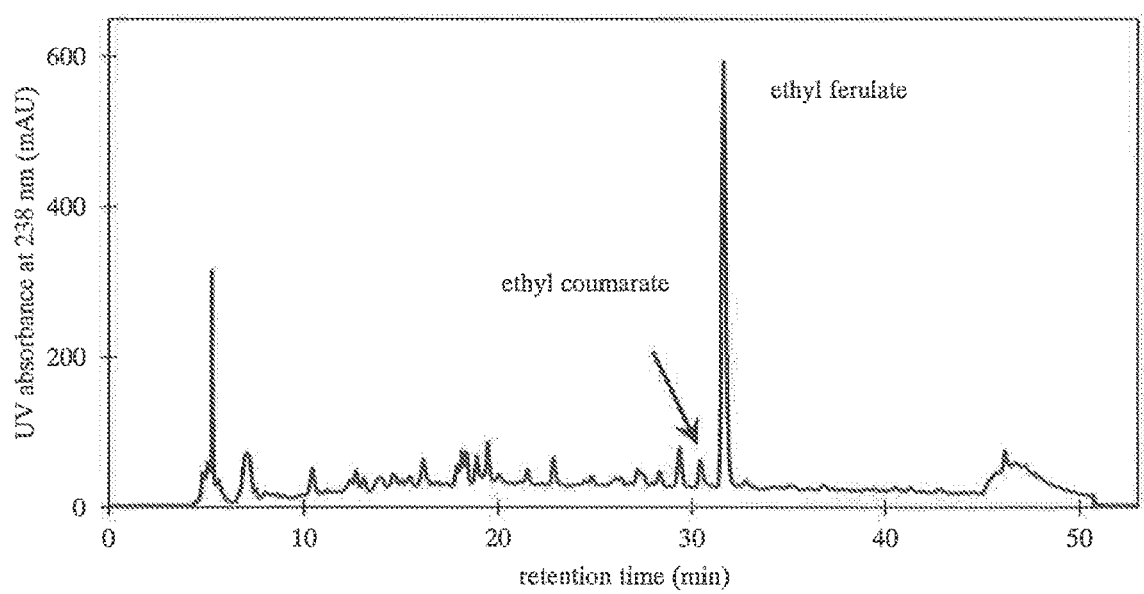
FIG. 5 illustrates the results of an HPLC/UV-vis chromatogram for the oil of Example 1.

In this example, 1.005 g of corn fiber that was previously dried at 100° C. for 24 hr was loaded into a 100 mL stirred batch reactor (Parr Instruments 2430) with 20 mL 200 proof anhydrous ethanol. The reactor was sealed and purged with 99.999% hydrogen (Airgas Hy UHP) four times by pressurizing the reactor to 17.2 bar and subsequently venting the pressure to ca. 3 bar. The reactor was pressurized to a final pressure of 34.5 bar. The temperature was increased to 200° C. at a ramp rate of 300° C. hr$^{-1}$ while the reactor was stirred at 200 rpm. The temperature was held for 12 hours before returning to room temperature. After reaction, the solvent and solids were filtered through filter paper (particle retention >11 μm) and rinsed with methanol to a total volume of 50 mL. The ethyl ferulate content of the liquid was analyzed by HPLC Method 1, as shown in FIG. 5. Ethyl coumarate and ethyl ferulate eluted at ca. 30.4 and 31.6 min, respectively. The yield of ethyl ferulate was determined to be 1.0% with respect to the total dry mass of corn fiber (assuming 8% moisture content of the biomass, dry mass=0.92*1.005 g=0.925 g).

Example 2

Example 2. Extraction of Methyl Ferulate and Methyl Coumarate from Miscanthus

Figure 6:
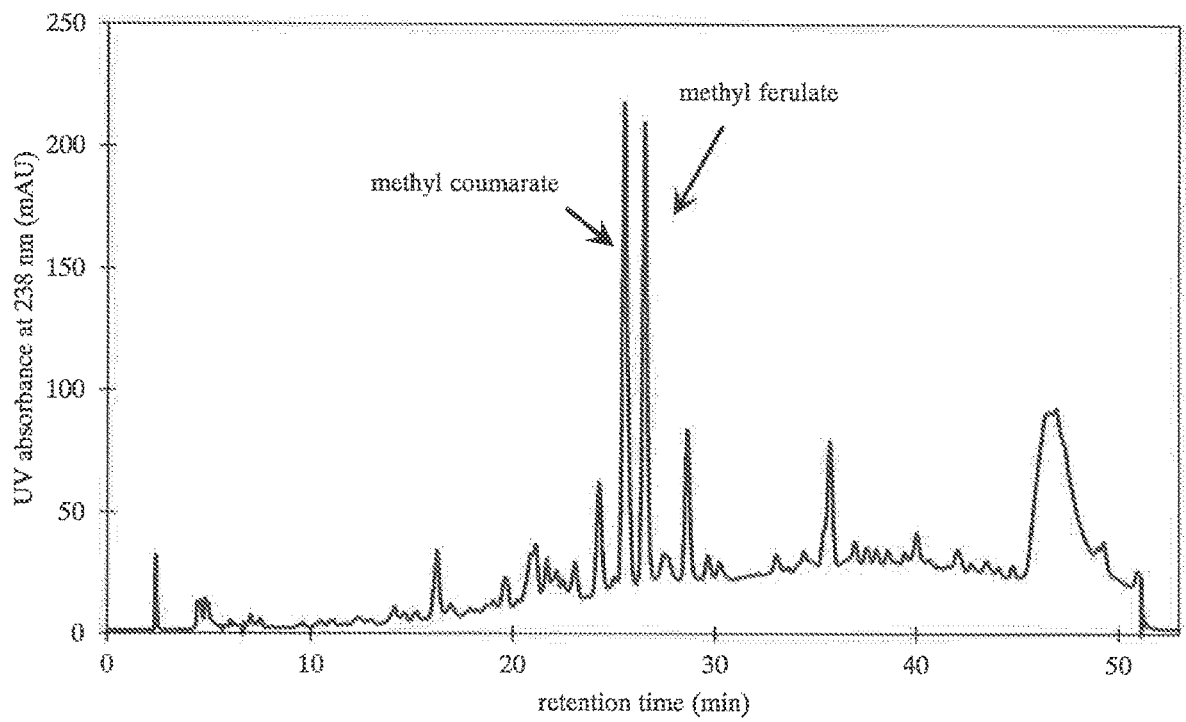
FIG. 6 illustrates the results of an HPLC/UV-vis chromatogram for the oil of Example 2.

In this example, 255.2 g of miscanthus was loaded into a 7.5 L stirred batch reactor (Parr Instruments 4550) with 4 L methanol. The reactor was sealed and purged with 99.999% argon (Airgas Ar UHP) four times by pressurizing the reactor to 7 bar and subsequently venting the pressure to ca. 2 bar. The reactor was pressurized to a final pressure of 7.6 bar. The temperature was increased to 200° C. at a ramp rate of 150° C. hr$^{-1}$ while the reactor was stirred at 200 rpm. The temperature was held for 12 hours before returning to room temperature. After reaction, the solvent and solids were filtered through a nylon bag (particle retention >75 m) and rinsed with methanol to a total volume of 3.2 L. The methyl ferulate and coumarate content of the liquid was analyzed by HPLC Method 1, as shown in FIG. 6. Methyl coumarate and methyl ferulate eluted at ca. 25.5 and 26.5 min, respectively. The yield of methyl ferulate and methyl coumarate were determined to be 0.5% and 3.9%, respectively, with respect to the total dry mass of miscanthus (assuming 8% moisture content of the biomass, dry mass=0.92*255.2 g=234.8 g).

Example 3

Example 3. Extraction of Ethyl Ferulate from Corn Fiber at 170° C.

Figure 7:
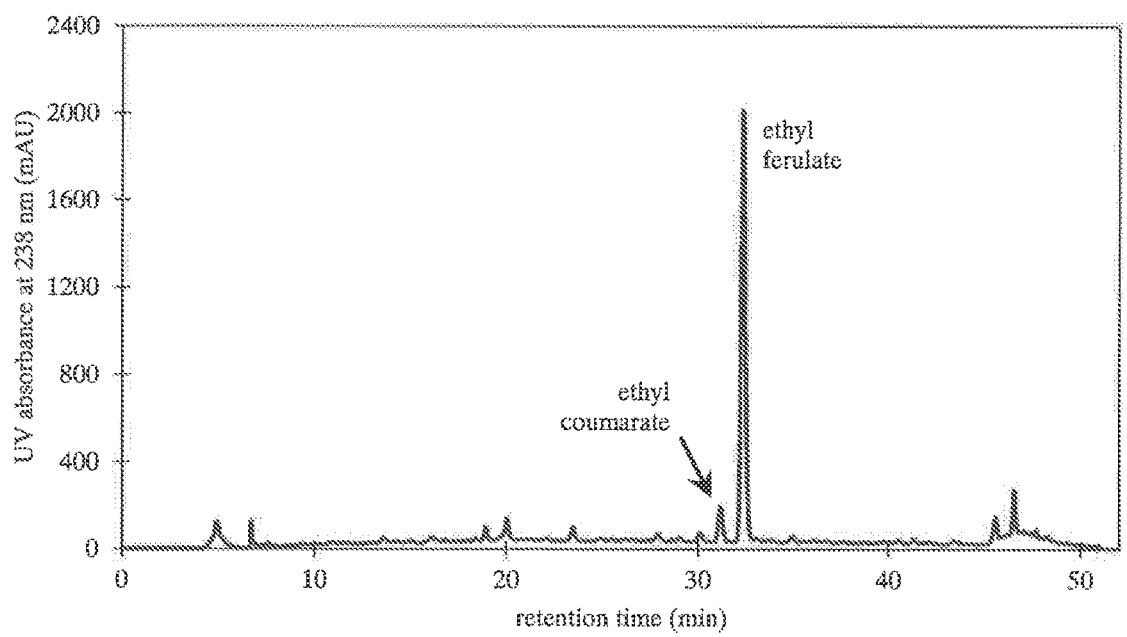
FIG. 7 illustrates the results of an HPLC/UV-vis chromatogram for the oil of Example 3.

In this example, 7.5 kg of corn fiber previously dried at 90° C. for 24 hr under vacuum was loaded into a 113.6 L stirred batch reactor with 60 L 200 proof anhydrous ethanol and 144 g NaOH. The reactor was sealed and purged with nitrogen 3 times by pressurizing the reactor to 7 bar and subsequently venting the pressure to ca. 2 bar. The reactor was filled with nitrogen to a final pressure of 1 bar. The temperature was increased to 170° C. at a ramp rate of 225° C. hr$^{-1}$ while the reactor was stirred at 600 rpm. The temperature was held for 12 hours before cooling to room temperature. After reaction, the solvent and the solids were filtered through a nylon filter bag and rinsed with 19 L ethanol. The ethanol oil was concentrated with a rotary evaporator to 3.1 kg. The ethyl ferulate content of the oil was analyzed by HPLC Method 1, as shown in FIG. 7. Ethyl coumarate and ethyl ferulate eluted at ca. 31.2 and 32.4 min, respectively. The yield of ethyl ferulate was determined to be 1.5% with respect to the total dry biomass (assumed to be 7.5 kg in this case because the fiber was dried immediately before processing).

Example 4

Example 4. Extraction of Ethyl Ferulate from Corn Fiber at 145° C.

Figure 8:
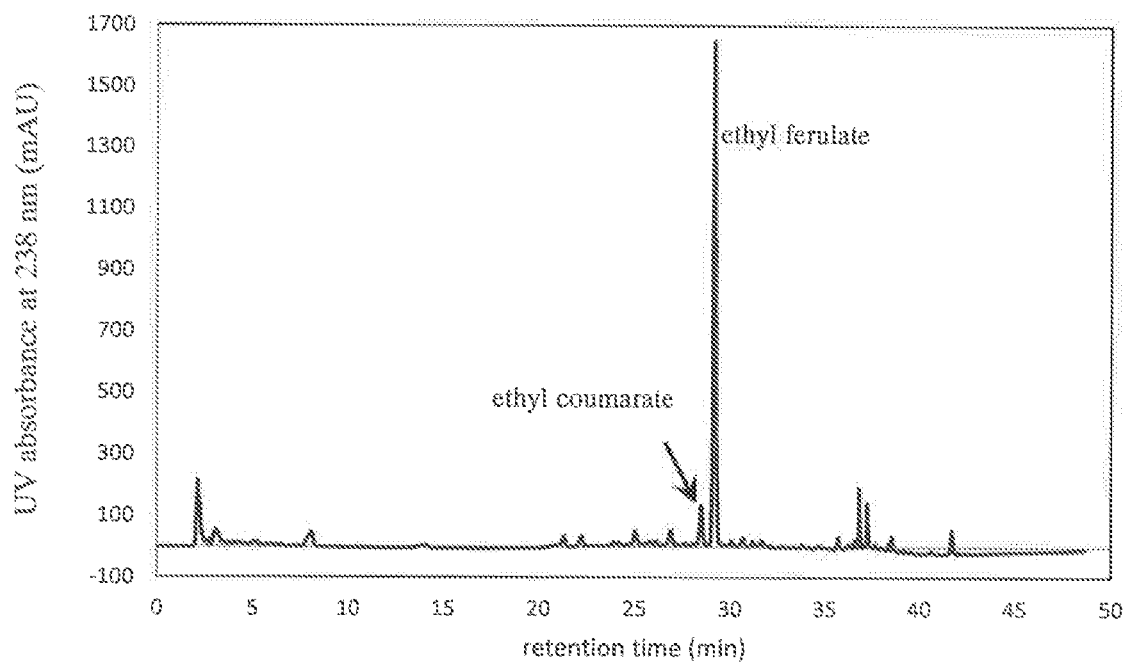
FIG. 8 illustrates the results of an HPLC/UV-vis chromatogram for the oil of Example 4.

In this example, 1.0 g of corn fiber that was previously dried at 100° C. for 24 hr was loaded into a 100 mL stirred batch reactor (Parr Instruments 2430) with 20 mL 200 proof anhydrous ethanol. To the reaction was added 32 mg NaOH. The reactor was sealed and purged with 99.999% argon (Airgas Ar UHP) four times by pressurizing the reactor to 17.2 bar and subsequently venting the pressure to ca. 3 bar. The reactor was pressurized to a final pressure of 3 bar with Argon gas. The temperature was increased to 145° C. at a ramp rate of 300° C. hr$^{-1}$ while the reactor was stirred at 200 rpm. The temperature was held at 145° C. for 12 hours before returning to room temperature. After reaction, the solvent and solids were filtered through filter paper (particle retention >11 μm) and rinsed with methanol to a total volume of 50 mL. The ethyl ferulate content of the liquid was analyzed by HPLC Method 2, as shown in FIG. 8. Ethyl coumarate and ethyl ferulate eluted at ca. 30.4 and 31.6 min, respectively. The yield of ethyl ferulate was determined to be 1.66% with respect to the total dry mass of corn fiber (assuming 8% moisture content of the biomass, dry mass=0.92*1.0 g=0.92 g).

Example 5

Example 5. Extraction of Ethyl Ferulate from Corn Fiber at 120° C.

Figure 9:
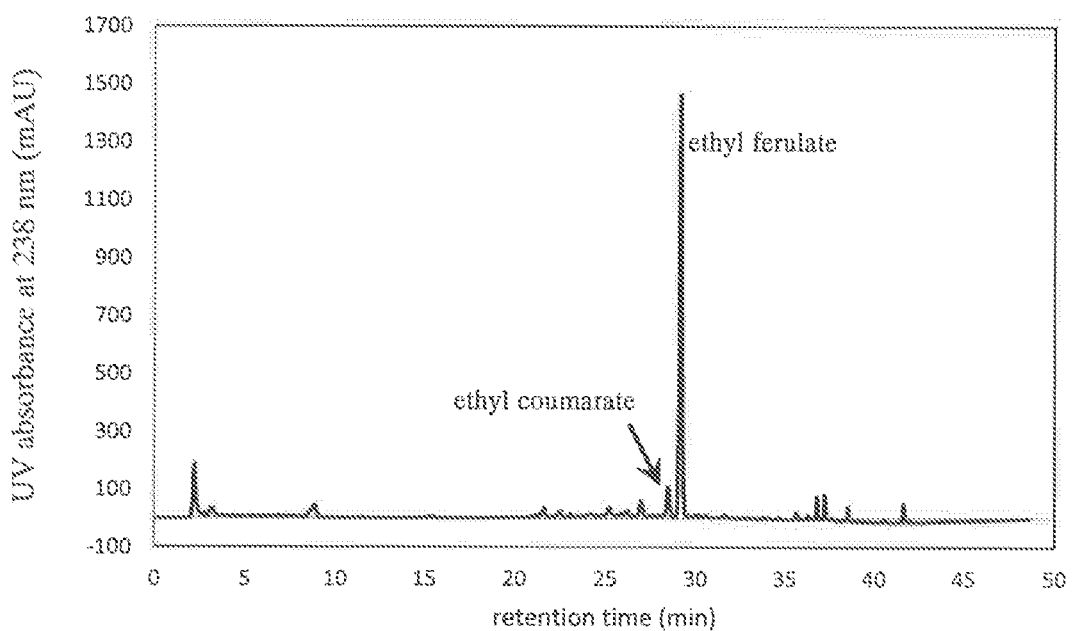
FIG. 9 illustrates the results of an HPLC/UV-vis chromatogram for the oil of Example 5.

In this example, 1.0 g of corn fiber that was previously dried at 100° C. for 24 hr was loaded into a 100 mL stirred batch reactor (Parr Instruments 2430) with 20 mL 200 proof anhydrous ethanol. To the reaction was added 32 mg NaOH. The reactor was sealed and purged with 99.999% argon (Airgas Ar UHP) four times by pressurizing the reactor to 17.2 bar and subsequently venting the pressure to ca. 3 bar. The reactor was pressurized to a final pressure of 3 bar with Argon gas. The temperature was increased to 120° C. at a ramp rate of 300° C. $hr^{-1}$ while the reactor was stirred at 200 rpm. The temperature was held at 120° C. for 12 hours before returning to room temperature. After reaction, the solvent and solids were filtered through filter paper (particle retention >11 m) and rinsed with methanol to a total volume of 50 mL. The ethyl ferulate content of the liquid was analyzed by HPLC Method 2, as shown in FIG. 9. Ethyl coumarate and ethyl ferulate eluted at ca. 30.4 and 31.6 min, respectively. The yield of ethyl ferulate was determined to be 1.52% with respect to the total dry mass of corn fiber (assuming 8% moisture content of the biomass, dry mass=0.92*1.0 g=0.92 g).

Example 6

Figure 10:
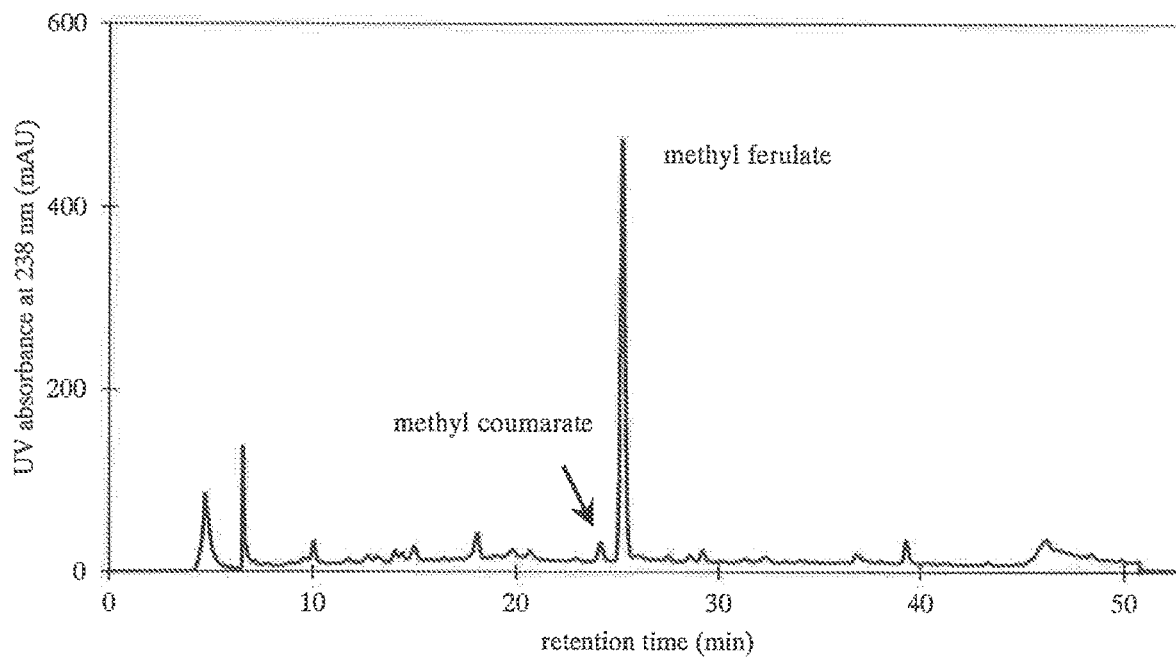
FIG. 10 illustrates the results of an HPLC/UV-vis chromatogram for the oil of example 6.
Figure 11:
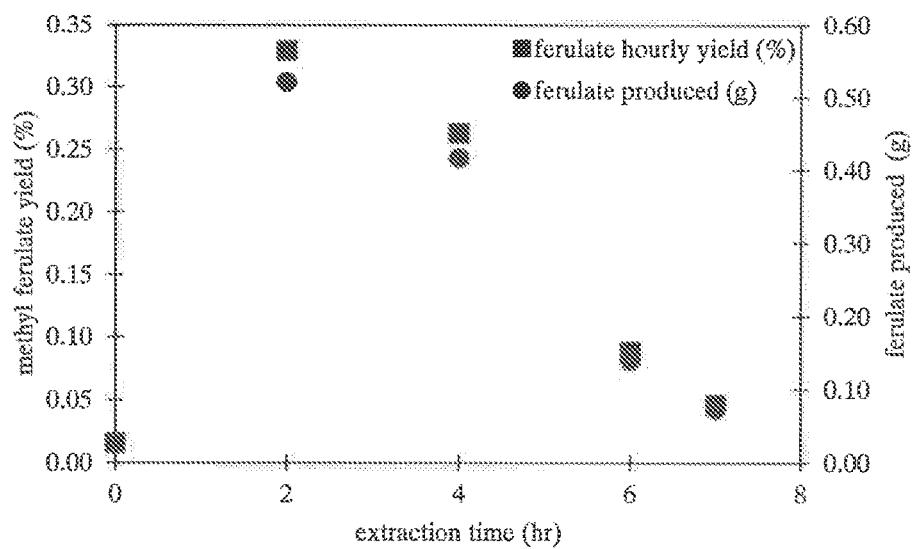
FIG. 11 illustrates the results of the yield of methyl ferulate on a dry mass basis per hour of Example 6.

Example 6. Extraction of Methyl Ferulate and Methyl Coumarate from a Continuous Reactor In this example, 172.3 g of corn fiber previously dried at 100° C. for 24 hr was loaded into a 1 L packed bed reactor which was insulated inside a furnace. The back pressure regulator was set to 7 bar, and the reactor was filled with methanol at a flow rate of 3 mL $min^{-1}$. The back pressure regulator was increased to 46.9 bar while the furnace temperature was ramped such that an internal thermocouple in contact with the corn fiber at the exit of the packed bed recorded a temperature of 200° C., which required 3 hr. The packed bed was maintained at 46.9 bar and 200° C. for 6 hr before the furnace was turned off and the methanol flow rate was increased to 10 mL $min^{-1}$ for 10 min to flush the corn fiber bed. The methanol flow was stopped and the reactor was cooled to room temperature overnight. Methanol from the system was collected in a reservoir with a total volume of 1.81 L. The methyl ferulate content of the oil was analyzed by HPLC Method 1, as shown in FIG. 10. Methyl coumarate and methyl ferulate eluted at ca. 24.2 and 25.3 min, respectively. The yield of methyl ferulate and methyl coumarate was determined to be 1.5% and 1.3%, respectively, with respect to the total dry biomass (assuming 8% moisture content of the biomass, dry mass=0.92*172.3 g=158.5 g). The hourly extraction of methyl ferulate and methyl coumarate is shown in FIG. 11. As shown in FIG. 11, time 0 hr corresponds to the first time the internal bed temperature at the exit was 200° C.

Example 7

Figure 12:
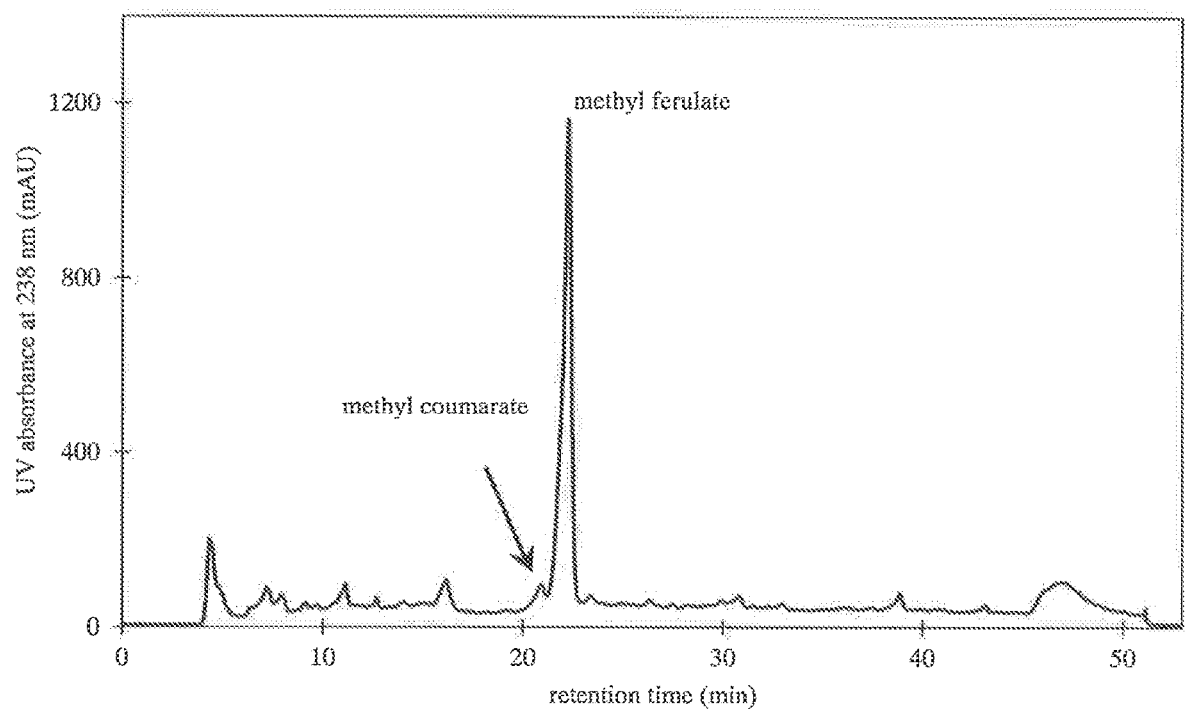
FIG. 12 illustrates the results of an HPLC/UV-vis chromatogram for the oil of Example 7.

Example 7. Extraction of Methyl Ferulate and Methyl Coumarate from Corn Bran In this example, 591 g of corn bran was loaded into a 7.5 L stirred batch reactor (Parr Instruments 4550) with 4.4 L methanol. The reactor was sealed and purged with 99.999% argon (Airgas Ar UHP) four times by pressurizing the reactor to 7 bar and subsequently venting the pressure to ca. 2 bar. The reactor was pressurized to a final pressure of 7.6 bar. The temperature was increased to 200° C. at a ramp rate of 150° C. $hr^{-1}$ while the reactor was stirred at 200 rpm. The temperature was held for 12 hours before returning to room temperature. After reaction, the solvent and solids were filtered through a nylon bag (particle retention >75 μm) and rinsed with methanol to a total volume of 3.8 L. The methyl ferulate and coumarate content of the liquid was analyzed by HPLC Method 1, FIG. 12. Methyl coumarate and methyl ferulate eluted at ca. 20.4 and 22.3 min, respectively. The yield of methyl ferulate was determined to be 2.3% with respect to the total dry mass of corn bran (assuming 8% moisture content of the biomass, dry mass=0.92*591 g=543.7 g).

Example 8

Example 8. Hydrolysis of Ethyl Ferulate to Ferulic Acid

Figure 13:
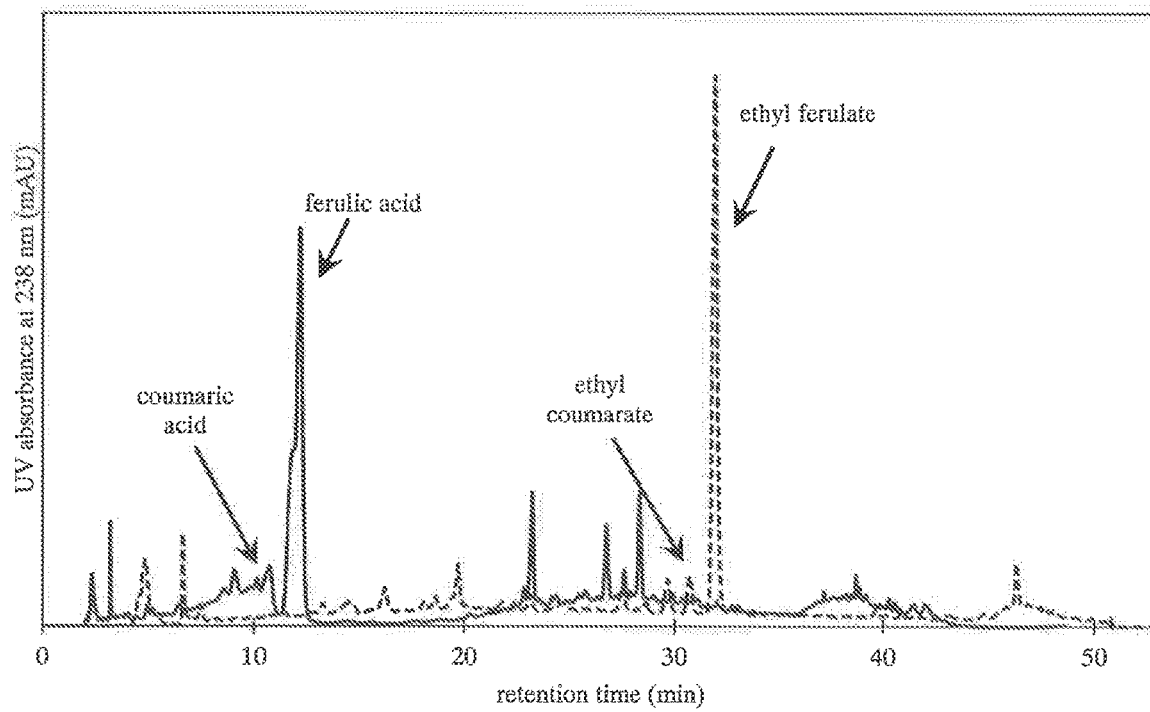
FIG. 13 illustrates the results of an HPLC/UV-vis chromatogram for a crude oil from Example 8 containing ethyl ferulate and ethyl coumarate and hydrolyzed crude oil.

In this example, 19.8 g of concentrated ethanol oil containing ethyl ferulate and ethyl coumarate extracted from corn fiber was added to 50 mL deionized water with 4 N NaOH. The oil was soluble in aqueous base. The solution was stirred in a round bottom and heated to 34° C. for 35 min, which hydrolyzed ethyl ferulate and ethyl coumarate to ferulic acid and coumaric acid. HPLC chromatograms for the concentrated ethanol oil (Method 1) and the hydrolyzed solution (Method 2) are shown in FIG. 13. No ethyl ferulate is present in the post hydrolysis solution, owing to the full conversion of ethyl ferulate to ferulic acid and ethyl coumarate to coumaric acid. The results are shown in FIG. 13. As illustrated, a HPLC/UV-vis chromatogram was recorded at 238 nm. The red, dashed lines show the results from Method 1 applied for crude oil containing ethyl ferulate and ethyl coumarate. The blue, solid lines show the results from Method applied for hydrolyzed crude oil. Ethyl coumarate and ethyl ferulate eluted at ca. 30.7 and 31.9 min, respectively. Coumaric acid and Ferulic acid eluted at ca. 9.8 and 12.2 min, respectively.

Example 9

Example 9. Corn Oil Removal

Figure 14:
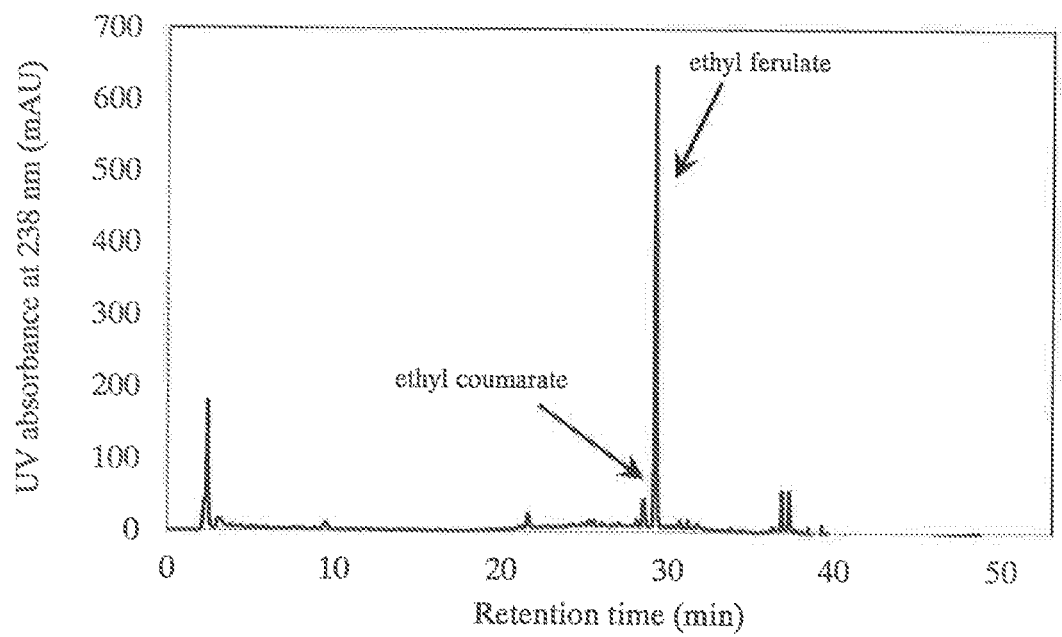
FIG. 14 illustrates the results of an HPLC/UV-vis chromatogram for the aqueous phase of Example 9 following corn oil removal.
Figure 15:
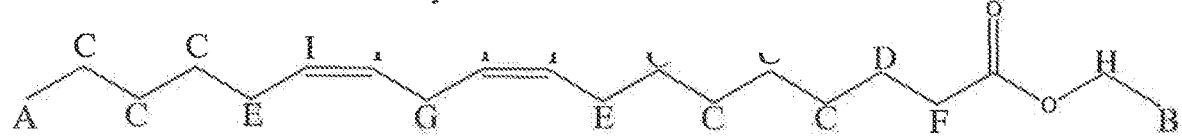
FIG. 15 illustrates the results of $^1$HNMR spectroscopy of the corn oil isolated in Example 9.
Figure 15:
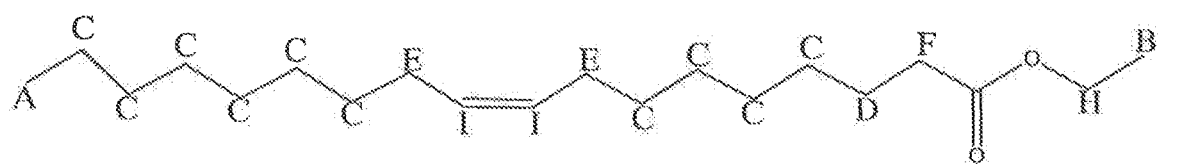
Figure 15:
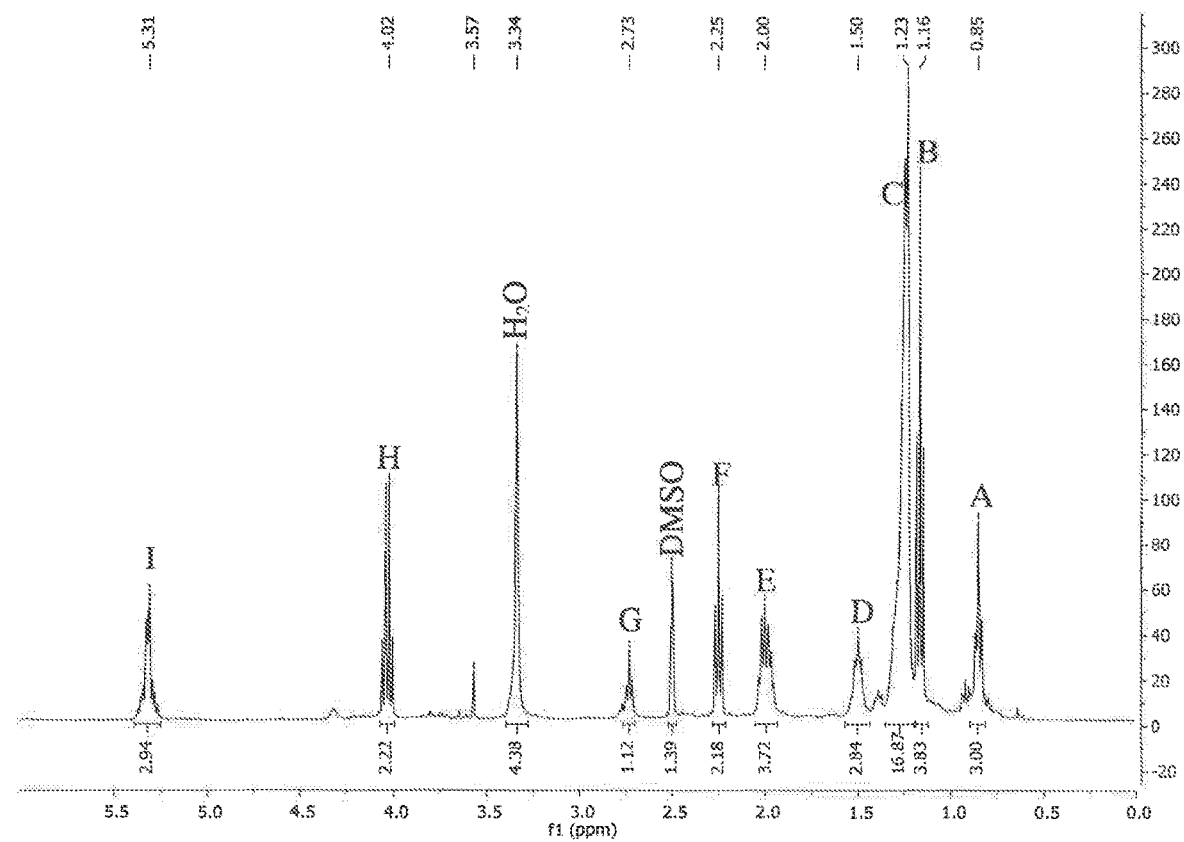

In this example, 500 g of concentrated ethanol oil containing ethyl ferulate and ethyl coumarate extracted from corn fiber was added to 1 L deionized water with 0.5 N NaOH. The oil was soluble in aqueous base. The aqueous solution was placed into a separatory funnel and washed with 330 mL hexanes. The hexanes was then removed from the separatory funnel and the aqueous solution was washed with 330 mL hexanes two additional times. In total 990 mL hexanes was used. The hexane extract was then placed in a round bottom flask and the hexanes removed with a rotary evaporator to yield liquid corn oil. Following extraction of the aqueous ethyl ferulate and ethyl coumarate solution with hexanes, the volume of the aqueous layer was 1.5 L and the ethyl ferulate and ethyl coumarate remained in the aqueous layer. HPLC analysis (Method 2) of the aqueous phase following hexane extraction confirmed that ethyl ferulate and ethyl coumarate remained in the aqueous layer as shown in FIG. 14. $^1$HNMR analysis of the corn oil using a Varian Unity Inova 400 MHz spectrometer was used to confirm that the corn oil is comprised of primarily the ethyl esters of oleic and linoleic acid as shown in FIG. 15.

Example 10

Example 10. Hydrolysis of Ferulate to Ferulic Acid

Figure 16:
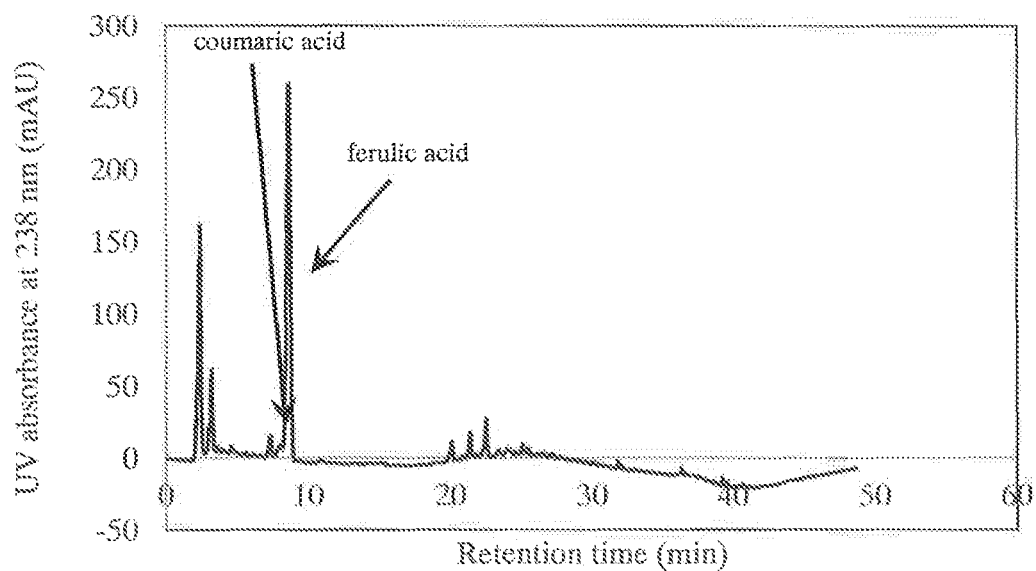
FIG. 16 illustrates the results of an HPLC/UV-vis chromatogram for the solution of Example 10 following hydrolysis.

In this example 1.9 L aqueous ethyl ferulate and ethyl coumarate solution from which corn oil had been previously extracted was used. An additional 32 g NaOH was added to the aqueous ethyl ferulate and ethyl coumarate solution increasing the total concentration of NaOH to 0.76 N. The resulting solution was heated to 60° C. and held at 60° C. for two hours, which hydrolyzed ethyl ferulate and ethyl coumarate to ferulic acid and coumaric acid. Following heating, HPLC analysis (Method 2) was used to confirm the complete hydrolysis of ethyl ferulate and ethyl coumarate to ferulic acid and coumaric acid as shown in FIG. 16.

Example 11

Example 11. Precipitation of Lignin and Polysaccharides

In this example 650 mL of aqueous ferulic acid and coumaric acid solution produced in Example 10 was added to 1.3 L water. The resulting solution was heated to 90° C. To the heated solution, 10 mL concentrated sulfuric acid was added dropwise over a time period of five minutes, acidifying the solution to pH 4.5. Following addition of the sulfuric acid, a solid precipitate was visible in the solution. The solution was filtered with a Buchner funnel and filter paper, separating the solid lignin and polysaccharide mixture from the aqueous ferulic acid and coumaric acid solution. The volume of the aqueous ferulic acid and coumaric acid solution was 1.85 L and the mass of the precipitated lignin/polysaccharide mixture was 20.7 g.

Example 12

Example 12. Extraction of Ferulic Acid into an Organic Solvent

In this example 1.04 L aqueous ferulic acid and coumaric acid solution from which lignin and polysaccharides had been precipitated, as described in Example 11, was used. The aqueous ferulic acid and coumaric acid solution was heated to 80° C. and 1.5 mL concentrated sulfuric acid was added to the solution. After addition of the sulfuric acid, the pH of the solution was reduced to pH 3. The solution was then added to a separatory funnel and extracted with 330 mL ethyl acetate. This extraction was repeated two additional times, with a total of 990 mL ethyl acetate used to extract the aqueous solution. Following extraction of the aqueous solution, the ethyl acetate samples were combined and condensed by rotary evaporation. Rotary evaporation of the ethyl acetate fraction yielded 9.1 grams of a dark oil which contained 2.7 g ferulic acid.

Example 13

Example 13. Crystallization of Ferulic Acid

Figure 17:
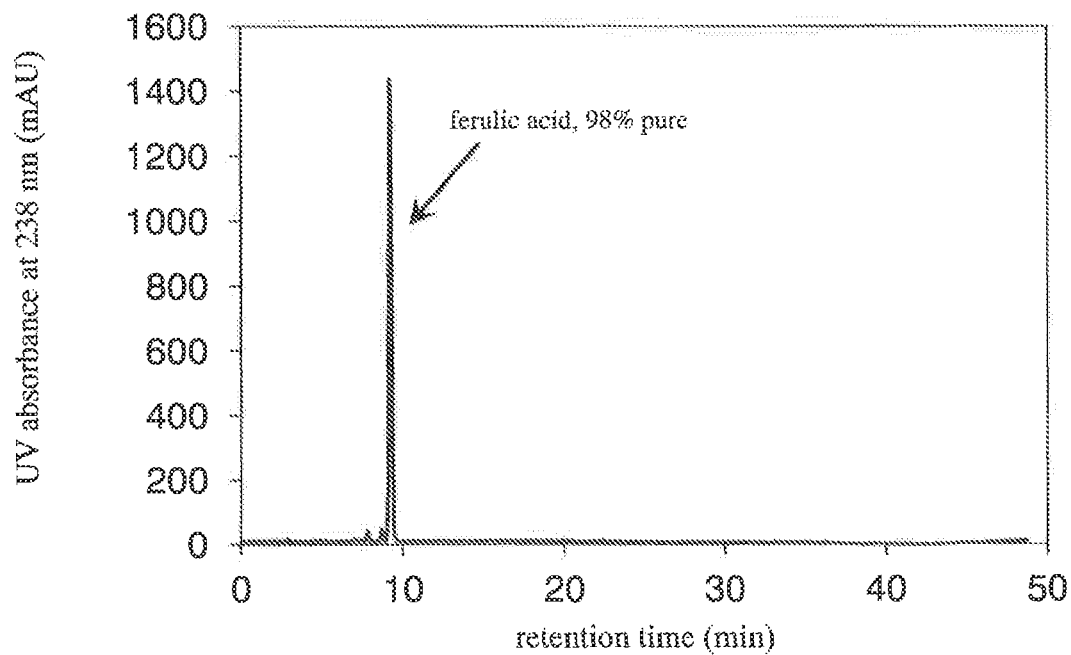
FIG. 17 illustrates the results of an HPLC/UV-vis chromatogram for Example 13 showing ferulic acid with a purity of greater than or equal to 98% pure.

In this example, 9.1 grams of an oil containing 2.7 g ferulic acid was used, this oil was the product of Example 12. 100 mL deionized water was added to the ferulic acid containing oil and the solution was heated to 100° C. and the ferulic acid was dissolved. The heated solution was filtered using a Buchner funnel and filter paper to remove solid impurities. The filter paper was rinsed with 20 mL deionized water which had been pre-heated to a temperature of 85° C. The aqueous filtrate was cooled to 5° C. and crystals of high purity ferulic acid precipitated from the solution over a time period of 12-18 hours. A HPLC chromatogram of ferulic acid with a purity of equal to or greater than 98% purity is shown in FIG. 17.

Having described the various systems and methods, various embodiments as disclosed herein can include, but are not limited to:

In a first aspect, an integrated process for the reactive separation of organic molecules from biomass comprises: a reaction step for the biomass, a simultaneous extraction step using a solvent, and a filtration step to recover the products, wherein the products comprise a ferulate or a coumarate.

In a second aspect, a reactive separation process for the separation of organic molecules including acidic esters, terpenoids, sterols, carbohydrates, and flavonoids from biomass comprises: a reaction step using a base in contact with the biomass, a simultaneous solvent extraction step using a solvent, and a filtration step to recover the products comprising the organic molecules.

A third aspect can include the process of any of the first or second aspects, wherein the products comprise at least one of: ferulate (ferulic acid ester), and coumarate (coumaric acid ester), wherein the products are extracted from the biomass in a pressurized stirred batch reactor using a liquid extraction solvent and the base in which the ferulate and the coumarate remain soluble and the insoluble solids are filtered from the liquid phase and washed.

A fourth aspect can include the process of any of the first to third aspects, wherein the reactor contains liquid and a pressurized gas consisting of nitrogen, argon, helium, or hydrogen, or their mixtures, or wherein the reactor contains a 100% inert atmosphere.

A fifth aspect can include the process of any of the first to fourth aspects, wherein the dry biomass is obtained from agricultural products.

A sixth aspect can include the process of any of the first to fifth aspects, wherein the biomass is mixed with a solvent containing 50-100% any aliphatic alcohols and 0-50% water.

A seventh aspect can include the process of any of the first to sixth aspects, wherein the extraction solvent is 100% ethanol or 100% methanol, or wherein the extraction solvent comprises a biologically obtained ethanol.

An eighth aspect can include the process of any of the first to seventh aspects, wherein the mass ratio of solvent to biomass is in the range of 4 to 30, or in the range of between 10 and 15.

A ninth aspect can include the process of any of the first to eighth aspects, wherein the base is any first or second group hydroxide, carbonate, bicarbonate, or ammonium hydroxide.

A tenth aspect can include the process of the ninth aspect, wherein the base is between 0-1 N, or about 0.04 N NaOH.

An eleventh aspect can include the process of any of the first to tenth aspects, wherein the reaction step is carried out in a reactor, and wherein the reactor is pressurized to 1-3 bar at room temperature, or about 1 bar.

A twelfth aspect can include the process of any of the first to eleventh aspects, wherein the reaction step is carried out in a reactor, and wherein the reactor is heated at 100-300° C. $hr^{-1}$ to a reaction temperature of between about 80-250° C., or wherein the heating rate is about 300° C. $hr^{-1}$.

A thirteenth aspect can include the process of the twelfth aspect, wherein the reactor is held at the reaction temperature for 1-15 hours, or about 12 hours.

A fourteenth aspect can include the process of any of the first to thirteenth aspects, wherein the reactor is stirred at a rate between about 100-600 rpm, or at about 200 rpm.

A fifteenth aspect can include the process of any of the first to fourteenth aspects, wherein the filtration step produces filtered solids, and wherein the filtered solids recovered from the reaction are washed with 50-150% the original volume of the extraction solvent used.

A sixteenth aspect can include the process of any of the first to fifteenth aspects, further comprising: diluting the products with an aqueous solution comprising a base to create a diluted product; contacting the diluted product with an organic solvent; extracting one or more organic molecules from the diluted product into the organic solvent to produce a rich organic phase and a purified product.

A seventeenth aspect can include the process of any of the sixteenth aspect, further comprising: removing the organic solvent from the rich organic phase to produce a oil phase and the organic solvent.

An eighteenth aspect can include the process of any of the first to seventeenth aspects, further comprising: combining the products with an aqueous base solution to form a hydrolysis mixture; heating the hydrolysis mixture; and hydrolyzing any ferulates to ferulic acid in the hydrolysis mixture in response to the heating.

A nineteenth aspect can include the process of any of the first to eighteenth aspects, further comprising: adding an acid to the products; acidifying the products in response to adding the acid to produce acidified products; precipitating one or more byproducts from the acidified products; and removing the one or more byproducts as solids from the acidified products, wherein a concentration of ferulic acid in the acidified products is greater after removing the one or more byproducts than prior to acidifying the products.

A twentieth aspect can include the process of the nineteenth aspect, further comprising: contacting the acidified products with an organic solvent after removing the one or more byproducts; extracting the ferulic acid from the acidified products using the organic solvent to form a rich organic solvent; removing the organic solvent from the rich organic solvent; and producing a solid ferulic acid in response to removing the organic solvent from the rich organic solvent.

A twenty first aspect can include the process of the twentieth aspect, further comprising: dissolving the solid ferulic acid in an aqueous solution to form dissolved ferulic acid; heating the dissolved ferulic acid; filtering the dissolved ferulic acid; removing one or more insoluble impurities from the dissolved ferulic acid using the filtering; and cooling the dissolved ferulic acid after removing the one or more insoluble impurities to produce purified solid ferulic acid.

A twenty second aspect can include the process of any of the twentieth or twenty first aspects, further comprising: purifying the ferulic acid using liquid chromotography.

In a twenty third aspect, a process to extract ferulate (ferulic acid ester) and coumarate (coumaric acid ester) from agricultural biomass in a packed bed reactor, wherein the process comprises: contacting the biomass with a solvent and a base in the packed bed reactor, wherein the agricultural biomass acts as the stationary bed.

A twenty fourth aspect can include the process of the twenty third aspect, wherein the solvent comprises an aliphatic alcohol, and the solvent is pumped through the reactor at a flow rate of between 1-10 mL min$^{-1}$, or at a flow rate between about 1.5-3 mL min$^{-1}$.

A twenty fifth aspect can include the the process of the twenty third or twenty fourth aspect, further comprising contacting the biomass with a base in the packed bed reactor with the solvent, wherein the base is any first or second group hydroxide, carbonate, bicarbonate, or ammonium hydroxide and has a concentration between 0-1 N, or about 0.04 N.

A twenty sixth aspect can include the process of any of the twenty third to twenty fifth aspects, wherein the packed bed reactor is pressurized to between about 13-30 bar, or to between about 13-20 bar.

A twenty seventh aspect can include the process of any of the twenty third to twenty sixth aspects, wherein the temperature of the packed bed reactor is heated at a rate of between about 100-300° C. hr$^{-1}$, or at a rate of about 300° C. hr$^{-1}$, to a desired temperature of between about 80-250° C.

A twenty eighth aspect can include the process of the twenty seventh aspect, wherein the reactor is held at the desired reactor temperature for 4-8 hours.

A twenty ninth aspect can include the process of any of the twenty third to twenty eighth aspects, wherein after an appropriate dwell time the reactor is cooled 20° C., and the solvent flow rate is increased to 10 mL min$^{-1}$ to flush the reactor zone into the collection container.

A thirtieth aspect can include the process of the first, second, or twenty third aspects in which the solids from the products are filtered from the liquid phase, and then the solvent is concentrated to a viscous oil using a rotary evaporator.

In a thirty first aspect, a process in which ferulate and coumarate containing oil, such as any oil obtained in one of the first to thirtieth aspects is suspended in water and extracted with hexanes followed by ethyl acetate, leaving the ferulate and coumarate in the ethyl acetate phase.

A thirty second aspect can include the process of the thirty first aspects in which the ethyl acetate phase is distilled in a short path distillation apparatus such as a Kugelrohr or wiped thin film evaporator at fractions up to 200° C.

In a thirty third aspect, a process in which the ferulate and coumarate, for example as obtained in any of the first to thirty second aspects, are hydrolyzed to ferulic acid under basic conditions.

A thirty fourth aspect can include the process of the thirty third aspect, wherein 2-20 mL of water are added per gram ferulate products.

A thirty fifth aspect can include the process of the thirty third or thirty fourth aspect, wherein the base includes any first or second group hydroxides such as sodium hydroxide or potassium hydroxide, carbonates, bicarbonates, or ammonium in a concentration of 0.1-10 N.

A thirty sixth aspect can include the process of any of the thirty third to thirty fifth aspects, wherein the solution is heated to 30-100° C.

A thirty seventh aspect can include the process of any of the thirty third to thirty sixth aspects, wherein the hydrolysis is carried out for 0.5-5 hours for complete conversion of ferulate to ferulic acid, and coumarate is converted to coumaric acid.

In the preceding discussion and in the claims, the terms "including" and "comprising" are used in an open-ended fashion, and thus should be interpreted to mean "including, but not limited to . . . ". At least one embodiment is disclosed and variations, combinations, and/or modifications of the embodiment(s) and/or features of the embodiment(s) made by a person having ordinary skill in the art are within the scope of the disclosure. Alternative embodiments that result from combining, integrating, and/or omitting features of the embodiment(s) are also within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). For example, whenever a numerical range with a lower limit, R1, and an upper limit, Ru, is disclosed, any number falling within the range is specifically disclosed. In particular, the following numbers within the range are specifically disclosed: $R=R1+k*(Ru-R1)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed. Use of the term "optionally" with respect to any element of a claim means that the element is required, or alternatively, the element is not required, both alternatives being within the scope of the claim. Use of broader terms such as comprises, includes, and having should be understood to provide support for narrower terms such as consisting of, consisting essentially of, and comprised substantially of. Accordingly, the scope of protection is not limited by the description set out above but is defined by the claims that follow, that scope including all equivalents of the subject matter of the claims. Each and every claim is incorporated as further disclosure into the specification and the claims are embodiment(s) of the present invention.

What is claimed is:

1. A process for a reactive separation of organic molecules from biomass comprising:
 a reaction step for the biomass, wherein the reaction step comprises contacting the biomass with a base, and extracting products from the biomass based on a reaction of the base with the biomass,
 a simultaneous extraction step using a solvent, wherein the solvent comprises an aliphatic alcohol, and wherein the extraction step comprises contacting the biomass with the solvent while contacting the biomass with the base,
 producing a slurry from the reaction step and the simultaneous extraction step;
 recovering a liquid product from the slurry, wherein the liquid product comprises a ferulate, a coumarate, ferulic acid, coumaric acid, or any combination thereof and a fatty acid ester; and
 removing the fatty acid ester from the liquid product, wherein removing the fatty acid ester from the liquid product comprises at least one of:
 1) removing the fatty acid ester from the liquid product by a liquid-liquid extraction with a base and an organic solvent to produce a purified liquid product comprising the coumarate, the ferulate, the ferulic acid, and coumaric acid, or any combination thereof;
 2) removing the fatty acid ester from the liquid product by a liquid-liquid extraction with an organic solvent to produce a purified liquid product comprising the coumarate, the ferulate, the ferulic acid, and coumaric acid, or any combination thereof; or
 3) concentrating the liquid product to a viscous oil and removing the fatty acid ester from the liquid product by liquid-liquid extraction with an organic solvent under basic conditions to produce a purified product comprising the coumarate, the ferulate, the ferulic acid, the coumaric acid, or any combination thereof.

2. The process of claim 1, wherein the ferulate comprises a ferulic acid ester, and wherein the coumarate comprises a coumaric acid ester.

3. The process of claim 1, wherein the products are extracted from the biomass in a pressurized stirred batch reactor or stirred batch reactor using a liquid extraction solvent and a base in which the ferulate and the coumarate remain, and wherein the reactor contains liquid and a gas consisting of nitrogen, argon, helium, or hydrogen, or their mixtures.

4. The process of claim 3, wherein a base is any first or second group hydroxide, carbonate, bicarbonate, or ammonium hydroxide, and wherein the base has a concentration between 0-1 N.

5. The process of claim 1, wherein the biomass is obtained from agricultural products.

6. The process of claim 1, wherein the solvent comprises 50-100% any aliphatic alcohols and 0-50% water, or wherein the extraction solvent is 100% aliphatic alcohol.

7. The process of claim 1, wherein a mass ratio of solvent: biomass is in a range of 4 to 30.

8. The process of claim 1, wherein the reaction step is carried out in a reactor, wherein the reactor is heated to a reaction temperature of between about 80-250° C., and wherein the reactor is held at the reaction temperature for 1-15 hours.

9. The process of claim 1,
 wherein the biomass comprises a solid;
 wherein recovering the liquid product comprises filtering the biomass to recover the liquid product, wherein the liquid product comprises the organic molecules, wherein the organic molecules comprise acidic esters, terpenoids, sterols, carbohydrates, and flavonoids; and
 hydrolyzing the liquid product under basic conditions to convert at least a portion of the acid esters to a corresponding acid.

10. The process of claim 9, wherein the products comprise at least one of: a ferulate, a ferulic acid ester, a coumarate, or a coumaric acid ester, and wherein the solvent comprises 50-100% any aliphatic alcohols and 0-50% water.

11. The process of claim 9, wherein a mass ratio of solvent to biomass is in a range of 4 to 30, and wherein the base is any first or second group hydroxide, carbonate, bicarbonate, or ammonium hydroxide.

12. The process of claim 9,
 wherein removing the fatty acid ester from the liquid product comprises: generating a rich organic phase comprising the fatty acid ester and the organic solvent and a purified product.

13. The process of claim 12, further comprising:
 removing the organic solvent from the rich organic phase to produce an oil phase and the organic solvent, wherein the oil phase has a phosphorus content of less than 250 ppm by mass and an oleic acid content of less than 3% by mass of the oil phase.

14. The process of claim 9, wherein hydrolyzing the liquid product under basic conditions comprises:
 combining the liquid product with an aqueous base solution to form a hydrolysis mixture;
 heating the hydrolysis mixture; and
 hydrolyzing any ferulates to ferulic acid in the hydrolysis mixture in response to the heating.

15. The process of claim 9, further comprising:
adding an acid to the liquid product after removing the fatty acid ester;
acidifying the liquid products in response to adding the acid to produce acidified products;
precipitating one or more byproducts from the acidified products; and
removing the one or more byproducts as solids from the acidified products, wherein a concentration of ferulic acid in the acidified products is greater after removing the one or more byproducts than prior to acidifying the products.

16. The process of claim 15, further comprising:
contacting the acidified products with an organic solvent after removing the one or more byproducts;
extracting the ferulic acid from the acidified products using the organic solvent to form a rich organic solvent;
removing the organic solvent from the rich organic solvent; and
producing a solid ferulic acid in response to removing the organic solvent from the rich organic solvent.

17. The process of claim 16, further comprising:
dissolving the solid ferulic acid in an aqueous solution to form dissolved ferulic acid;
heating the dissolved ferulic acid;
filtering the dissolved ferulic acid;
removing one or more insoluble impurities from the dissolved ferulic acid using the filtering; and
cooling the dissolved ferulic acid after removing the one or more insoluble impurities to produce purified solid ferulic acid.

18. The process of claim 17, further comprising:
purifying the ferulic acid using liquid chromotography.

19. The process of claim 1:
wherein the reaction step and simultaneous extraction step occur in a packed bed reactor, wherein the biomass acts as a stationary bed in the packed bed reactor; and
wherein recovering the liquid product comprises: extracting the ferulate, the fatty acid ester, and the coumarate from the biomass in the packed bed reactor as the liquid product; and
hydrolyzing the liquid product under basic conditions to convert at least a portion of the ferulate to ferulic acid.

20. The process of claim 19, wherein the solvent comprises 50-100% any aliphatic alcohols and 0-50% water, or wherein the solvent is 100% aliphatic alcohol, and wherein the solvent is pumped through the packed bed reactor.

21. The process of claim 19, wherein the base is any first or second group hydroxide, carbonate, bicarbonate, or ammonium hydroxide and has a concentration between 0-1 N.

22. The process of claim 19, wherein the packed bed reactor is heated to a reaction temperature of between about 80-250° C., and held at desired temperature for 1-15 hours.

23. The process of claim 22, wherein after heating the packed bed reactor, the method further comprises: cooling the packed bed reactor, and increasing a solvent flow rate to flush the biomass in the packed bed reactor into a collection container.

24. The process of claim 1, wherein removing the fatty acid ester from the liquid product comprises:
diluting the liquid product with an aqueous solution comprising a base to create a diluted product;
contacting the diluted product with an organic solvent, wherein the organic solvent is at least partially immiscible with the diluted product; and
extracting one or more organic molecules from the diluted product into the organic solvent to produce a rich organic phase and a purified product.

25. The process of claim 1, further comprising:
acidifying the liquid product; and
precipitating lignin, polysaccharides, or both from the liquid product based on the acidifying.

26. The process of claim 25, further comprising:
using chromatography to increase a purity of ferulic acid in the liquid product.

27. The process of claim 26, further comprising:
performing a hot filtration and precipitation process to purify the ferulic acid in the liquid product.

28. The process of claim 1, further comprising:
hydrolyzing the liquid product under basic conditions to convert at least a portion of the ferulate to ferulic acid.

* * * * *